(12) United States Patent
Westphal et al.

(10) Patent No.: US 6,504,081 B1
(45) Date of Patent: Jan. 7, 2003

(54) METHODS AND USES FOR TRANSPOSON-BASED GENE TARGETING

(75) Inventors: Christoph H. Westphal, Boston, MA (US); Philip Leder, Chestnut Hill, MA (US)

(73) Assignee: President and Fellow of Harvard College, Cambridge, MA (US)

( * ) Notice: Subject to any disclaimer, the term of this patent is extended or adjusted under 35 U.S.C. 154(b) by 0 days.

(21) Appl. No.: 09/089,940

(22) Filed: Jun. 8, 1998

Related U.S. Application Data

(60) Provisional application No. 60/049,523, filed on Jun. 13, 1997.

(51) Int. Cl.⁷ ............................................. C12N 15/00
(52) U.S. Cl. ............................. 800/25; 800/21; 435/6; 435/320.1; 435/463; 435/473; 435/445; 536/23.4; 536/23.5; 536/23.7; 536/24.31; 536/24.33
(58) Field of Search ............................ 435/320.1, 6, 8, 435/455, 463, 473; 800/3, 4, 7, 8, 9, 13, 14, 21, 23, 25; 536/24.31, 24.33, 23.4, 23.5, 23.7

(56) References Cited

U.S. PATENT DOCUMENTS

| | | | | |
|---|---|---|---|---|
| 5,464,764 A | | 11/1995 | Capecchi et al. ............... 435/6 |
| 5,487,992 A | | 1/1996 | Capecchi et al. ............... 435/6 |
| 5,523,226 A | * | 6/1996 | Wheeler ................... 435/240.2 |
| 5,532,158 A | * | 7/1996 | Suzuki et al. ................ 435/354 |
| 5,545,527 A | * | 8/1996 | Stevens et al. ................. 435/6 |
| 5,627,059 A | | 5/1997 | Capecchi et al. ............. 800/21 |
| 5,631,153 A | * | 5/1997 | Capecchi et al. ............... 435/6 |
| 5,677,170 A | | 10/1997 | Devine et al. ............ 435/320.1 |
| 5,707,821 A | * | 1/1998 | Rydell et al. .................. 435/18 |
| 5,714,667 A | * | 2/1998 | Waterhouse et al. ........... 800/11 |
| 5,843,772 A | * | 12/1998 | Devine et al. ............ 435/320.1 |
| 5,888,774 A | * | 3/1999 | Delcuve ..................... 435/69.6 |

FOREIGN PATENT DOCUMENTS

| WO | WO 97/2003 | * | 6/1997 | ................. 435/325 |
|---|---|---|---|---|

OTHER PUBLICATIONS

Arig et. al.; A 15–base pair (bp) palindromic inseertion associated with a 3–bp deletion in exon 10 of the gp91–phox gene . . . chronic granulomatous disease, 1995, Hum Genet 96: 6–8.*

Asselbergs et. al.; Shuttle vectors conferring hydromycin B resistance to E. coli and and to mammalian cells, 1992, Molecular Biology Reports 17: 61–70.*

Bradley et al. Bio/technology 10: 534–539, see entire document, especially paragraph bridging pp. 537 and 538, May 1992.*

Seamark. Reprod. Fertil. Dev. 6: 653–657, see entire documen, especially p. 654, col. 2, paragraph 3; and abstract, 1994.*

Mullins et al. (Journal of Clinical Investigation 98(11): S37–S40 See especially p. S39, 1996.*

Braks et al., "Dissociation of the Complex Between the Neuroendocrine Chaperone 7B2 and Prohormone Concertase PC2 is Not Associated With proPc2 Maturation," Eur. J. Biochem. 238: 505–510, 1996.

Braks et al., "Structural Organization of the Gene Encoding the Neuroendocrine Chaperone 7B2," Eur. J. Biochem 236: 60–67, 1996

Braks and Martens, "The neuroendocrine chaperone 7B2 can enhance in vitro PoMC cleavage by prohormone convertase PC2," FEBS Lett. 371: 154–158, 1995.

Braks and Martens, "7B2 is a Neuroendocrine Chaperone that Transiently Interacts with Prohormone Convertase PC2 in the Secretory Pathway," Cell 78:263–273; 1994.

Capecchi M.R., "The New Mouse Genetics: Altering the Genome by Gene Targeting," Trends Genet. 5: 70–76, 1989.

Corral et al., "An MII–AF9 fusion gene made by homologous recombination causes acute leukemia in chimeric mice: A method to create fusion oncogenes," Cell 85: 853–861, 1996.

Devine and Boeke, "Efficient intergration of artificial transposons to plasmid targets in vitro: a useful tool for DNA mapping, sequencing and genetic analysis," Nucleic Acids Research 22: 3765–3772, 1994.

Deng et al., "Mice Lacking p21 $^{(CIP1/WAP1)}$ Undergo Normal Development, But Are Defective in G1 Checkpoint Control," Cell 82: 675–684, 1995.

Hoekstra, M.F., "Responses to DNA damage and regulation of cell cycle checkpoints by the ATM protein kinase family," Current Opinion in Genetics & Development 7: 170–175, 1997.

Martens, G.J.M., "Cloning and Sequence Analysis of Human Pituitary cDNA Encoding the Novel Polypeptide 7B2," FEBS Lett. 234: 160–164, 1998.

(List continued on next page.)

Primary Examiner—James Ketter
Assistant Examiner—Richard Schnizer
(74) Attorney, Agent, or Firm—Clark & Elbing LLP

(57) ABSTRACT

The present invention provides methods which greatly facilitate the rapidity in which cells and transgenic animals with targeted genes may be generated. The invention hastens the investigation of cells and transgenic animals bearing lowered expression of the targeted gene product, a truncated targeted gene product, a fusion protein of the targeted gene and exogenous DNA, or the expression of a different gene from the locus of the targeted gene whose product has reduced expression levels.

Also disclosed is a transgenic animal having Cushing's disease. Also disclosed are diagnostic methods for detecting patients with endocrine disorders, and methods for treating or alleviating the symptoms of endocrine disorders.

32 Claims, 12 Drawing Sheets

OTHER PUBLICATIONS

Meiner et al., "Disruption of the acyl–CoA: Cholesterol Acytransferase Gene in Mice: Evidence Suggesting Multiple Cholesterol Esterification Enzymes in Mammals," Proc. Natl. Acad. Sci. USA 93: 14041–14046, 1996.

Morgan et al., "Transposon tools for recombinant DNA manipulation: Characterization of transcriptional regulators from yeast, Xenopus, and Mouse," Proc. Natl. Acad. Sci. USA 93: 2801–2806, 1996.

Seidah and Chretien, "Proprotein and Prohormone Convertases of the Subtilisin Family," Trends Endocrinol. Metabol. 3: 133–140, 1992.

Steiner et al., "The New Emymology of Precursor Processing Endoproteases," J. Biol. Chem. 267: 23435–23438, 1992.

Tybulewicz et al., "Neonatal Lethality and Lymphopenia in Mice with a Homozygous Disruption of the c–abl Proto–Oncogene," Cell 85:1153–1163, 1991.

Wang et al., "The Mouse formin (Fmn) Gene: Genomic Structure, Novel Exons, and Genetic Mapping," Genomics 39: 303–311, 1997.

Westphal and Leder, "Transposon–generated 'knock out and knock in' gene–targeting constructs for use in mice," Current Biology 7: 530–533, 1997.

Westphal et al., "Genetic interactions between atm and p53 influence cellular proliferation and irradiation–induced cell cycle checkpoints," Cancer Research 57: 1664–1667, 1997.

Westphal et al., "atm and p53 cooperate in apoptosis and suppression of tumorigenesis, but not in resistance to acute radiation toxicity," Nature Genetics 16: 397–401, 1997.

Zhu et al., "Involvement of a Polyproline Helix–Like Structure in the Interaction of 7B2 with Prohormone Convertase 2," J. Biol. Chem. 271: 23582–23587, 1996.

Zhu et al., "Internal Cleavage of the Inhibitory 7B2 Carboxyl–Terminal Peptide by PC2: A Potential Mechanism for its Inactivation," Proc Natl. Acad. Sci. USA 93: 4919–4924, 1996.

Lindberg et al., "Enymatic Characterization of Immunopurified Prohormone Convertase 2: Potent Inhibition by a 7B2 Peptide Fragment," Biochemistry 34: 5486–5493, 1995.

Zhu and Lindberg., "7B2 Facilitates the Maturation of proPC2 in Neuroendocrine Cells and is Required for the Expression of Ezymatic Activity," J. Cell. Biol. 129: 1641–1650, 1995.

GenBank Accession No. X94303.

Devine et al., "transposon–based strategy for sequencing repetitive DNA in eukaryotic genomes," Genome Research 7: 551–563, 1997.

McCormick et al., "Expression of human apolipoprotein B90 in transgenic mice," Journal of Biological Chemistry 269: 24284–24289, 1994.

Waldbieser et al., "Cloning and characterization of the rat complementary deoxyribonucleic acid and gene encoding the neuroendocrine peptide 7B2," Endocrinology 128: 3228–3236, 1991.

* cited by examiner

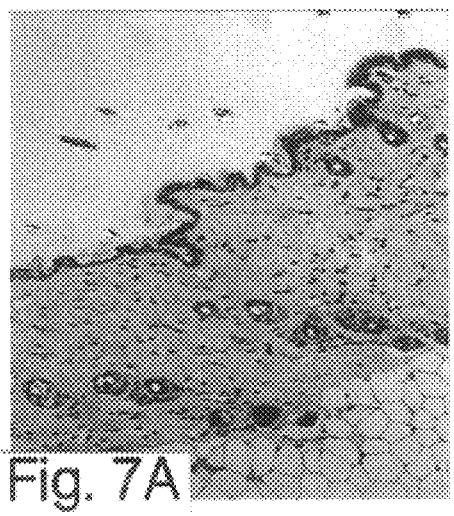
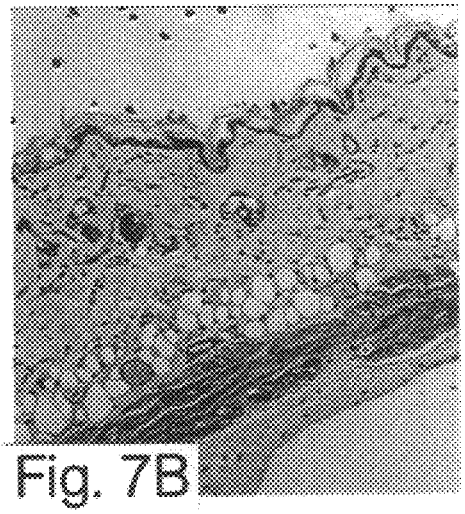
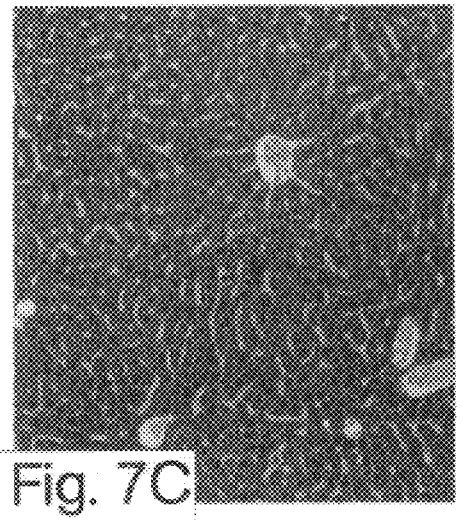
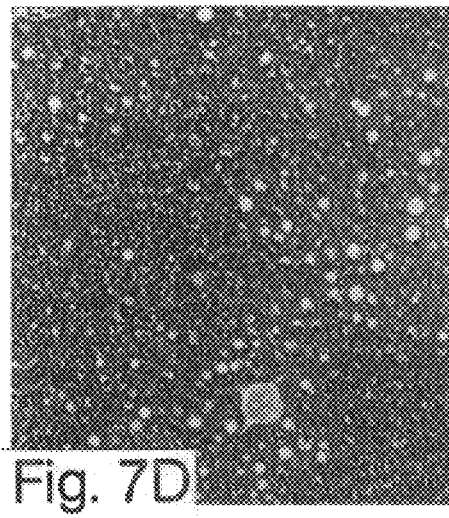
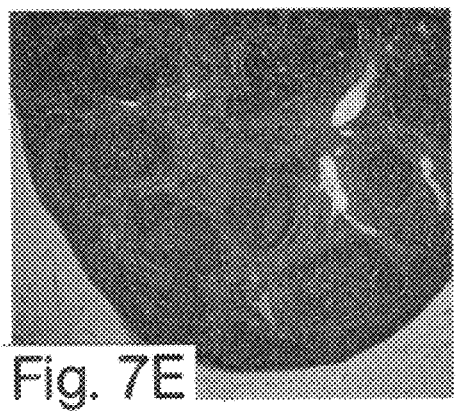
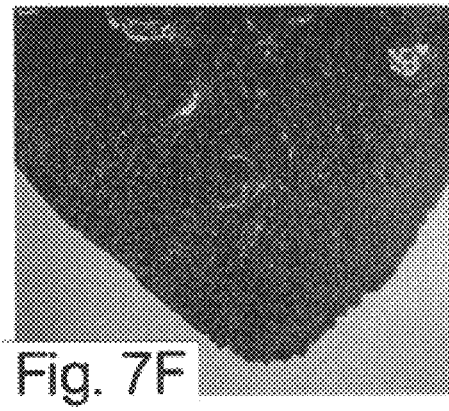

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

ACTAGA                                                                         6

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

CAACATTCCT GTTCACCGCG GTGGCGGCCG C          31

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

AGTTTTCCCA AGAGGACAGG          20

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

TTCTTCCCAC GCTGCAGGG          19

METHODS AND USES FOR TRANSPOSON-BASED GENE TARGETING

CROSS REFERENCE TO RELATED APPLICATION

This application claims benefit from United States provisional application, Ser. No. 60/049,523, which was filed Jun. 13, 1997.

BACKGROUND OF THE INVENTION

The invention relates to gene targeting for use, e.g., in the creation of transgenic, non-human mammals.

Gene targeting is a process whereby a specific gene, or a fragment of that gene, is altered. This alteration of the targeted gene may result in a change in the level of RNA or protein that is encoded by that gene, or the alteration may result in the targeted gene encoding a different RNA or protein than the untargeted gene. The targeted gene may be studied in the context of a cell, or, more preferably, in the context of a transgenic animal.

Transgenic animals are among the most useful research tools in the biological sciences. These animals have an heterologous (i.e., foreign) gene, or gene fragment, incorporated into their genome that is passed on to their offspring. Although there are several methods of producing transgenic animals, the most widely used is microinjection of DNA into single cell embryos. These embryos are then transferred into pseudopregnant recipient foster mothers. The offspring are then screened for the presence of the new gene, or gene fragment. Potential applications for transgenic animals include discovering the genetic basis of human and animal diseases, generating disease resistance in humans and animals, gene therapy, drug testing, and production of improved agricultural livestock.

SUMMARY OF THE INVENTION

In general, the invention features methods and uses for transposon-mediated gene targeting which greatly enhance the insertion and detection of desired genes in genomic exons by homologous recombination. The invention also features diagnostic methods for endocrine disorders, as well as methods and reagents for treating endocrine disorders.

In a first aspect, the invention provides a method for targeting heterologous DNA to integrate into an exon of a eukaryotic cell. The method includes, first, generating a pool of bacteria containing plasmids into which have been randomly integrated a transposon including heterologous DNA; second, isolating from the pool a bacterium which contains a plasmid into which the transposon is integrated into a copy of the exon on the plasmid by assessing PCR amplification products generated from the pool using primers specific for the exon; third, introducing the plasmid of the bacteria into the cell under conditions that promote homologous recombination; and, fourth, screening genomic DNA of the cell for integration of the heterologous DNA into the exon of the cell.

In one embodiment of the first aspect of the invention, the transposon bears at its extremities recognition sequences of a first rare-cutting restriction endonuclease that is absent in the exon. In another embodiment, the heterologous DNA, or portion thereof, encodes a selectable marker protein. The heterologous DNA, or portion thereof, may additionally encode a second protein, or polypeptide fragment thereof. In another embodiment, the marker protein is a prokaryotic selectable marker protein, which may be replaced by a eukaryotic selectable marker protein via the recognition sequences of the first rare-cutting restriction endonuclease. The prokaryotic selectable marker protein may be additionally replaced with DNA, or a portion thereof, encoding a second protein, or polypeptide fragment thereof.

In another embodiment of this aspect, the exon copy or portion thereof has at its borders destroyed recognition sequences of a second rare-cutting restriction endonuclease. In another embodiment, the genomic DNA is digested with the second rare-cutting restriction endonuclease. In yet another embodiment, the screening is carried out by Southern blot analysis of the genomic DNA with a detectable probe specific for the exon, or with a detectable probe external to the exon. The screening may also be carried out by PCR amplification of the genomic DNA with primers specific for the exon, or with primers external to, but surrounding the exon such that the PCR product includes the exon.

In a preferred embodiment of the first aspect of the invention, the insertion of the heterologous DNA into the exon results in a reduced level of expression of the protein encoded by the gene of the exon. The insertion of the heterologous DNA into the exon may also result in the expression of a truncated protein encoded by the gene of the exon, expression of a fusion protein encoded by the gene of the exon and the heterologous DNA, or portion thereof, or expression of a product, which may be a fusion protein, encoded by the heterologous DNA, or portion thereof.

In a second aspect, the invention provides a method for making a transgenic, non-human vertebrate animal containing heterologous DNA by first producing an embryonal cell of the non-human vertebrate animal with a targeted exon by first, generating a pool of bacteria containing plasmids into which have been randomly integrated a transposon including heterologous DNA; second, isolating from the pool a bacterium which contains a plasmid into which the transposon is integrated into a copy of the exon on the plasmid by assessing PCR amplification products generated from the pool using primers specific for the exon; third, introducing the plasmid of the bacteria into the embryonal cells under conditions that promote homologous recombination; and fourth, screening genomic DNA of the embryonal cells to identify an embryonal cell in which there has occurred integration of the heterologous DNA into the exon. The identified embryonal cell is then grown to generate the transgenic animal.

In one embodiment of the second aspect of the invention, the transposon bears at its extremities recognition sequences of a first rare-cutting restriction endonuclease that are absent in the exon. In another embodiment, the heterologous DNA, or portion thereof, encodes a selectable marker protein. The heterologous DNA, or portion thereof, additionally encodes a second protein, or polypeptide fragment thereof.

In another embodiment, the marker protein is a prokaryotic selectable marker protein which may be replaced by a eukaryotic selectable marker protein via the recognition sequences of the first rare-cutting restriction endonuclease. In another embodiment, the prokaryotic selectable marker protein is additionally replaced with DNA, or a portion thereof, encoding a second protein, or polypeptide fragment thereof.

In another embodiment, the exon copy or portion thereof has at its borders destroyed recognition sequences of a second rare cutting restriction endonuclease. Genomic DNA may be digested with the second rare-cutting restriction endonuclease. In another embodiment, the screening is carried out by Southern blot analysis of the genomic DNA with a detectable probe specific for the exon, or with a detectable probe external to the exon. The screening may also be carried out by PCR amplification of the genomic DNA with primers specific for the exon, or with primers external to, but surrounding the exon such that the PCR product includes the exon.

In a preferred embodiment of this aspect of the invention, the animal expresses a reduced level of the protein encoded by the gene of the exon. In another embodiment, the animal expresses a truncated protein encoded by the gene of the exon. In another embodiment, the animal expresses a fusion protein product encoded by the gene of the exon and the heterologous DNA, or portion thereof. In another embodiment, the animal expresses a product, which may be a fusion protein, encoded by the heterologous DNA, or portion thereof.

In a third aspect, the invention features a transposon that includes a selectable marker cassette including the selectable marker operably linked to a promoter, or hybrid thereof, capable of expressing the marker in both eukaryotic and prokaryotic cells. In a preferred embodiment of this aspect of the invention, the selectable marker is both a prokaryotic and eukaryotic selectable marker. In another embodiment of this aspect of the invention, the cassette is flanked by the recognition sequences of one or more rare-cutting restriction endonucleases. Most preferably, the transposon of this aspect of the invention is used to integrate a targeted gene, or exon thereof, on a plasmid.

In a fourth aspect, the invention features a eukaryotic cell containing an endogenous exon into which there is integrated a transposon including DNA encoding a selectable marker.

In a fifth aspect, the invention provides a method for making a transgenic non-human vertebrate animal by providing an embryonal cell of the non-human vertebrate animal that includes an endogenous exon into which there is integrated a transposon including DNA encoding a selectable marker, and then growing the cell to produce the transgenic animal.

In a sixth aspect, the invention features a transgenic non-human mammal having an abnormal genotype that gives rise to one or more symptoms of Cushing's disease. In various embodiments, the mammal may have a disruption in an endogenous 7b2 gene, and the disruption may result in a reduced level of normal 7b2 protein. In another embodiment, the mammal is a mouse.

In a seventh aspect, the invention features a nucleic acid vector that includes nucleic acid capable of undergoing homologous recombination with an endogenous 7b2 gene, where the homologous recombination results in a disruption in the coding sequence of the endogenous 7b2 gene. In one embodiment, the disruption results in a reduced level of normal 7b2 protein.

In an eighth aspect, the invention features a eukaryotic cell containing an endogenous 7b2 gene into which there is integrated a transposon that includes DNA encoding a selectable marker.

In a ninth aspect, the invention features a method for diagnosing a mammal for an endocrine disorder that involves measuring 7b2 gene expression in a sample from the mammal, where abnormal expression is an indication that the mammal has an endocrine disorder or an increased likelihood of developing an endocrine disorder. Preferably, the mammal is a human.

In various embodiments of the ninth aspect of the invention, the abnormal expression is a reduced expression and the endocrine disorder is a hypercortisolism disorder (e.g., Cushing's disease), or the abnormal expression is a reduced expression and the endocrine disorder is a hypoglycemic disorder. In other embodiments, the abnormal expression is an increased expression and the endocrine disorder is a hypocortisolism disorder (e.g., Addison's disease), or the abnormal expression is an increased expression and the endocrine disorder is a hyperglycemic disorder (e.g., diabetes). In other embodiments, the expression is measured by assaying the amount of 7b2 polypeptide in the sample or by assaying the amount of 7b2 RNA in the sample.

In a tenth aspect, the invention features a method for diagnosing a mammal for an endocrine disorder or an increased likelihood of developing an endocrine disorder that involves isolating a sample of nucleic acid from the mammal and determining whether the nucleic acid includes a mutation in a 7b2 gene, where the presence of the mutation is an indication that the mammal has an endocrine disorder or has an increased likelihood of developing an endocrine disorder. Preferably, the mammal is a human.

In various embodiments of the tenth aspect of the invention, the mutation results in a reduced level of expression of the 7b2 gene and the endocrine disorder is a hypercortisolism disorder (e.g., Cushing's disease), or the mutation results in a reduced level of expression of the 7b2 gene and the endocrine disorder is a hypoglycemic disorder. In other embodiments, the mutation results in an increased level of expression of the 7b2 gene and the endocrine disorder is a hypocortisolism disorder (e.g., Addison's disease), or the mutation results in an increased level of expression of the 7b2 gene and the endocrine disorder is a hyperglycemic disorder (e.g., diabetes).

In an eleventh aspect, the invention features a method for determining whether a compound is potentially useful for treating or alleviating the symptoms of an endocrine disorder that includes the steps of: (a) providing a cell including a reporter gene operably linked to the promoter from a 7b2 gene; (b) contacting the cell with the compound; and (c) measuring the expression of the reporter gene, where a change in the level of the expression in response to the compound indicating that the compound is potentially useful for treating or alleviating the symptoms of an endocrine disorder.

In a twelfth aspect, the invention features a method for determining whether a compound is potentially useful for treating or alleviating the symptoms or an endocrine disorder that includes the steps of: (a) providing a cell expressing a 7b2 gene; (b) contacting the cell with the compound; and (c) monitoring the expression of the 7b2 gene, where a change in the level of the expression in response to the compound indicating that the compound is potentially useful for treating or alleviating the symptoms of an endocrine disorder.

In various embodiments of the eleventh and twelfth aspects of the invention, the change is a decrease and the endocrine disorder is a hypercortisolism disorder (e.g., Cushing's disease), or the change is a decrease and the endocrine disorder is a hypoglycemic disorder. In other embodiments, the change is an increase and the endocrine disorder is a hypocortisolism disorder (e.g., Addison's disease), or the change is an increase and the endocrine disorder is a hyperglycemic disorder (e.g., diabetes). In yet other embodiments, the 7b2 gene is from a mammal (e.g., a human or a mouse).

As used herein, by "protein" or "polypeptide" is meant any chain of amino acids, regardless of length or posttranslational modification (e.g., glycosylation or phosphorylation).

By "exon" is meant a region of a gene which includes sequences which are used to encode the amino acid sequence of the gene product.

By "knock-out" is meant an alteration in the nucleic acid sequence that reduces the biological activity of the polypeptide normally encoded therefrom by at least 80% compared to the unaltered gene. The alteration may be an insertion, deletion, frameshift mutation, or missense mutation. Preferably, the alteration is an insertion or deletion, or is a frameshift mutation that creates a stop codon.

By "plasmid" is meant a circular strand of nucleic acid capable of autosomal replication in plasmid-carrying bacteria. The term includes nucleic acid which may be either DNA or RNA and may be single- or double-stranded. The plasmid of the definition may also include the sequences which correspond to a bacterial origin of replication.

By "rare-cutting restriction endonuclease" is meant a restriction endonuclease whose recognition sequences are located at least 5,000 base pairs apart in the genomic DNA of a mammal. Such restriction endonucleases include, without limitation, SpeI, NotI, AscI, and PacI.

By "destroyed recognition sequence" is meant the recognition sequence of a restriction endonuclease which has been destroyed such that the sequence is no longer recognized or cleaved by the restriction endonuclease. One means of generating a destroyed recognition sequence is to ligate cleaved ends of recognition sequences from two different restriction endonucleases. For example, a SpeI fragment may be ligated to an XbaI fragment creating ligated DNA having the sequence of 5' ACTAGA 3' (SEQ ID NO: 1), which is not recognized by either SpeI or XbaI.

By "operably linked" is meant that a gene and a regulatory sequence are connected in such a way as to permit expression of the gene product under the control of the regulatory sequence.

By "selectable marker" is meant a gene product which may be selected for or against using chemical compounds, especially drugs. Selectable markers often are enzymes with an ability to metabolize the toxic drugs into non-lethal products. For example, the pac (puromycin acetyl transferase) gene product can metabolize puromycin, the dhfr gene product can metabolize trimethoprim (trnp) and the bla gene product can metabolize ampicillin (amp). Selectable markers may convert a benign drug into a toxin. For example, the HSV tk gene product can change its substrate, FIAU, into a lethal substance. A preferred selectable marker is one which may be utilized in both prokaryotic and eukaryotic cells. The neo gene, for example, metabolizes and neutralizes the toxic effects of the prokaryotic drug, kanamycin, as well as the eukaryotic drug, G418.

By "reporter gene" is meant any gene which encodes a product whose expression is detectable. A reporter gene product may have one of the following attributes, without restriction: fluorescence (e.g., green fluorescent protein), enzymatic activity (e.g., lacZ or luciferase), or an ability to be specifically bound by a second molecule (e.g., biotin or an antibody-recognizable epitope).

By "transgenic" is meant any animal which includes a nucleic acid sequence which is inserted by artifice into a cell and becomes a part of the genome of the animal that develops from that cell. Such a transgene may be partly or entirely heterologous to the transgenic animal. Although transgenic mice represent a preferred embodiment of the invention, other transgenic mammals including, without limitation, transgenic rodents (for example, hamsters, guinea pigs, rabbits, and rats), and transgenic pigs, cattle, sheep, and goats are included in the definition.

By "transposon" or "transposable element" is meant a linear strand of DNA capable of integrating into a second strand of DNA which may be linear or may be a circularized plasmid. Transposons often have insertion sequences, or remnants thereof, at their extremities, and are able to integrate into sites within the second strand of DNA selected at random, or nearly random. However, only one transposon may integrate into a second strand of DNA-following insertion of a transposon, the second strand of DNA becomes "transposition-incompetent." Preferred transposons have a short (e.g., less than ten) base pair repeat at either end of the linear DNA.

By "endocrine disorder" is meant a disorder affecting the endocrine system, resulting in an abnormally increased or reduced production of an endocrine hormone. Endocrine hormones include, without limitation, cortisol, corticosterone, insulin, and glucagon. Exemplary endocrine disorders include hypercortisolism (such as Cushing's disease), hypocortisolism (such as Addison's disease), hypoglycemia, and hyperglycemia (such as diabetes).

BRIEF DESCRIPTION OF THE DRAWINGS

FIGS. 7A and 7B are two photographs (20×) of the skin of wild-type (FIG. 7A) and 7b2 null (FIG. 7B) mice. The skin of a 7b2 null mouse (FIG. 7B) was atrophic, hyperkeratotic, and showed a marked epidermal thinning when compared to the skin of a wild-type mouse (FIG. 7A).

FIGS. 7C and 7D are two photographs (20×) of the livers of wild-type (FIG. 7C) and 7b2 null (FIG. 7D) mice. The liver of a 7b2 null mouse (FIG. 7D) was found to lack lobular architecture and showed fat vacuolation when compared to the liver of a wild-type mouse (FIG. 7C).

FIGS. 7E and 7F are two photographs (5×) of the spleens of wild-type (FIG. 7E) and 7b2 null (FIG. 7F) mice. Note the splenic myeloid atrophy in the 7b2 null (FIG. 7F) as compared to the wild type spleen (FIG. 7E).

DETAILED DESCRIPTION

The present invention describes a novel approach for generating gene-targeting constructs and generating trangenic animals using these constructs. In a simple in vitro reaction using a commercially available transposon and integrase, we have generated random insertional events in a knock-out vector containing thymidine kinase juxtaposed with mouse genomic DNA of interest. Transpositional events were selected via an antibiotic marker within the transposon. Specific, desired insertions into exonic sequences were subsequently screened for by bacterial colony PCR. Ligation of a neomycin resistance cassette into unique transposon sites within the exon of interest completed the gene-targeting vector, which was shown to undergo homologous recombination in mouse embryonic stem cells. This approach allowed, within a matter of days, the generation of a completed construct ready for transfection into embryonic stem cells from a starting genomic clone. This is a general approach that is applicable for insertional "knock-out" and "knock-in" constructs, and allows targeting of different exons contained within the same genomic clone, independent of convenient restriction endonuclease recognition sites. Using this technique, a number of constructs for the same or different genes may be produced simultaneously.

Transposon-mediated Generation of Mouse "Knock-out" Vectors

The conventional technique for generating a "knock-out" mouse entails placing a genomic fragment of interest into a vector for fine mapping, followed by cloning of two genomic arms around a neomycin resistance cassette in a vector containing thymidine kinase (Tybulewicz et al., Cell 61: 1153–1163, 1991). Depending upon skill and luck, this conventional technique generally requires one to two months for the generation of each construct. The single "knock-out" construct is then transfected into embryonic stem cells, which are subsequently subjected to positive (using G418) and negative (using FIAU) selection, allowing the selection of cells which have undergone homologous recombination with the knock-out vector. This approach leads to inactivation of the gene of interest (Capecchi, M. R., Trends Genet. 5: 70–76, 1989).

In the transposon-based gene targeting approach of the present invention, a genomic fragment containing an exonic sequence of interest was cloned into a vector containing nucleic acid sequences encoding thymidine kinase and a number of unique restriction endonuclease recognition sites at the edge of the multiple cloning site. FIGS. 1A–1D represent an outline of our transposon-mediated technique for gene targeting.

Figure 1A:
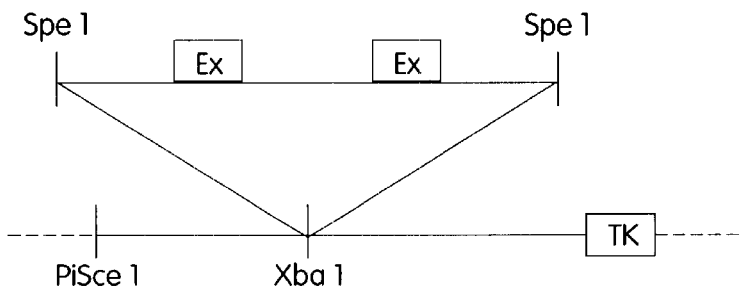
FIG. 1A is a schematic diagram illustrating the cloning of a representative SpeI genomic clone into an XbaI site of a targeting vector, resulting in the destruction of the genomic SpeI sites.
Figure 1B:
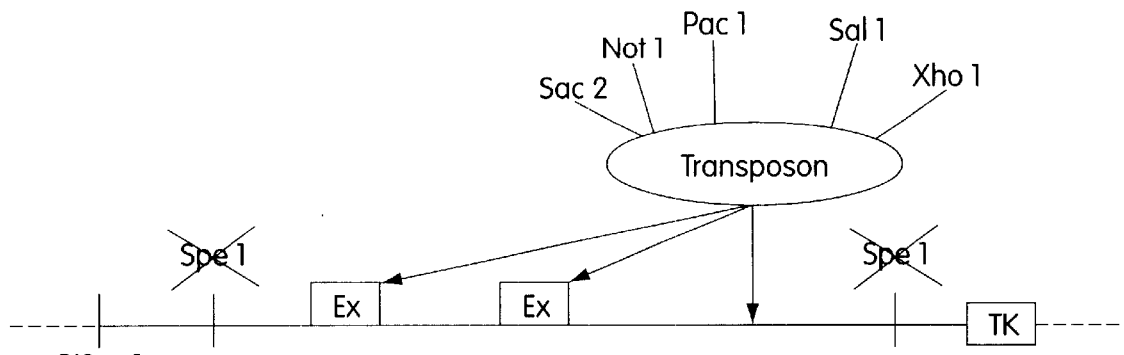
FIG. 1B is a schematic diagram representing an in vitro transposition reaction where the transposon inserts randomly into the targeting vector.

As a first step shown in FIG. 1A, restriction endonuclease recognition sites at the edge of a genomic clone of interest were destroyed (in the case illustrated here, a genomic SpeI fragment was cloned into an XbaI site of the targeting vector, thereby destroying the genomic SpeI sites). In the second step, as shown on FIG. 1B, a simple in vitro transposition reaction led to the random integration of a transposon into the genomic clone. The in vitro transposition reaction was carried out following the manufacturer's protocol (ABI, Perkin-Elmer Corp., Norwalk, Conn.). Briefly, 200 ng of transposon, 2 units of integrase, 1 μg of target plasmid, integrase buffer, and water were incubated at 30° C. for 1 hour. The reaction was stopped by incubation in 0.25 M EDTA, 1% SDS, and 5 µg/mL proteinase K for 15 minutes at 65° C. After phenol extraction, the product was precipitated with ammonium acetate and isopropanol, washed in 70% ethanol, and resuspended in 10 µL of water. 1 µL of this product was then electroporated into highly competent bacterial cells, which were then plated on selective medium containing 75 µg/mL of ampicillin and trimethoprim, since the CWKO vector contains an ampicillin (AMP) resistance gene (bla) and the integrated transposon contains the trimethoprim (TMP) resistant gene (dhfr). A typical reaction yielded 100–300 colonies per µL, or 1,000–3,000 amp/tmp resistant transposon-bearing colonies from total 10 µL transposition reaction. These colonies became apparent on AMP/TMP agarose plates 12–15 hours after electroporation. The transposon bore the recognition sequences for a number of rare cutting restriction endonucleases at its extremities, some of which are indicated in FIG. 1B. Thousands of unique, individual transposition events can be recovered as distinct, doubly-resistant colonies from a typical reaction (Devine and Boeke et al., Nuc. Acid. Res. 22: 3765–3774, 1994). The desired events (i.e., transpositions into the exon of interest) were discerned via a colony PCR screen using oligonucleotides homologous to exonic DNA.

Screening by colony PCR was carried out according to the following protocol. Single bacterial colonies were dipped into a master mix containing 0.4 µM primers, 0.2 mM dNTPs, 1x PCR buffer, Taq polymerase, and water. Primers used in this PCR were specific for genomic DNA. Samples were heated to 94° C. for 5 minutes, and then subjected to 30 cycles of 45 seconds 94° C., 30 seconds 55° C., and 1 minute 72° C. After dipping into the PCR master mix, colonies were touched to a master plate, which was incubated at 37° C. while PCR and gel analysis was performed. After completion of the PCR reaction in 2.5 hours, 1.5% agarose gels were loaded with a multichannel pipettor and run out with markers, to discern the desired transposition events. Setting up 300 PCR reactions, running the PCR program, and loading and analyzing gels was completed in six to eight hours. Colonies found to be positive for the desired transposition event by PCR were picked from the master plate and proliferated in miniprep format for eight hours. Hence, sticky-end ligation of the PGK neo$^c$ bpA neo cassette into the targeted exon and subsequent sequencing of the construct was completed in two days. Completed constructs were sequenced using a standard protocol (Perkin-Elmer Corp., Norwalk, Conn.) and analyzed on an ABI 377 automated sequencer.

Figure 1C:
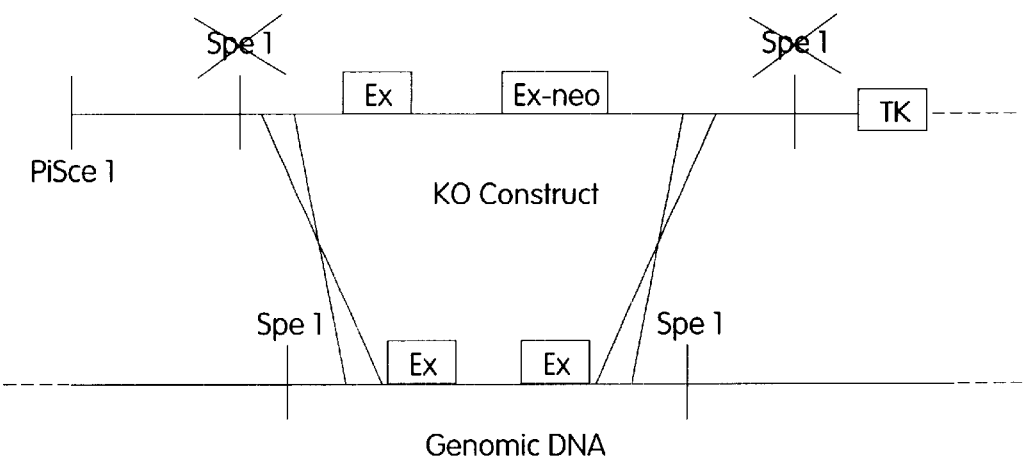
FIG. 1C is a schematic diagram representing a homologous recombination event between the transposon-bearing targeting vector and genomic DNA, such that the external SpeI sites are reconstituted.

Ligation of a neomycin resistance cassette into the unique transposon enzyme sites (see FIG. 1B) completed the generation of the gene-targeting construct. Neomycin resistance facilitated the selection of homologous recombination events based on regaining external enzyme sites, as depicted in FIG. 1C, and recombinants were verified by Southern blot analysis. Only those ES cells which had undergone homologous recombination regained the original SpeI restriction endonuclease recognition sites at the edge of the targeted exon at defined distances from the probe. The desired homologous recombinants may then be independently verified by an external probe, if desired.

Figure 1D:
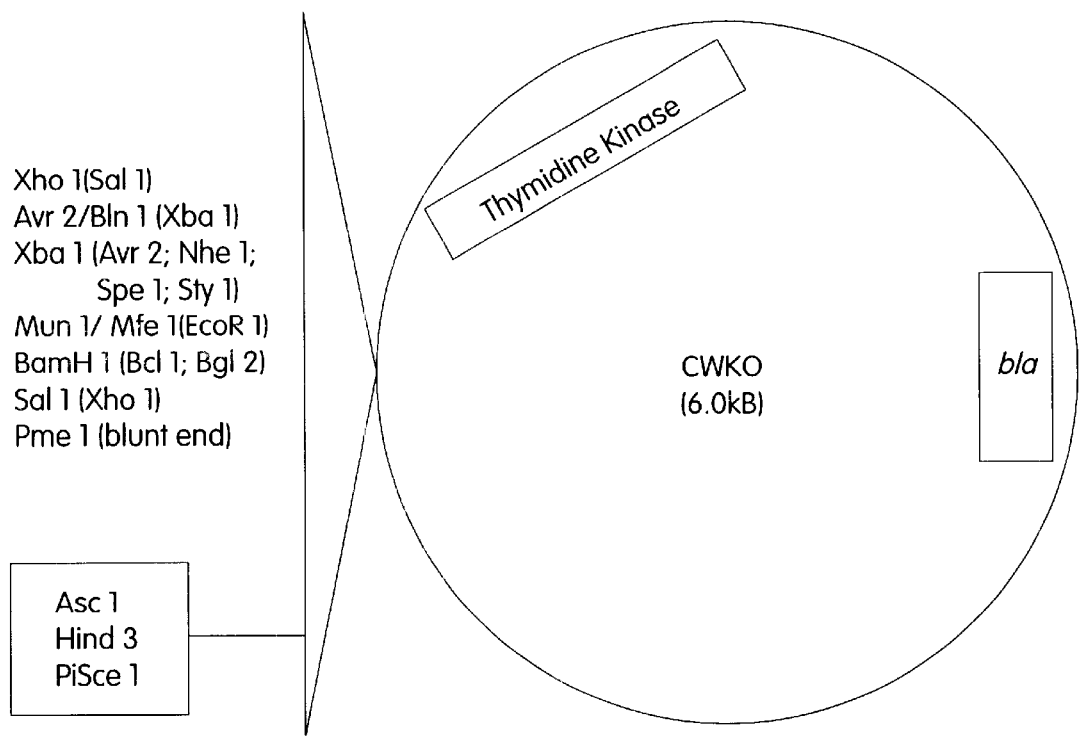
FIG. 1D is a schematic diagram of a map of the targeting vector CWKO.

FIG. 1D is a schematic drawing (not drawn to scale) of the vector, CWKO, used for this study, wherein all unique sites are listed. To generate the CWKO vector, the pSL301 Superlinker plasmid (commercially available from Invitrogen) was modified in the following manner: HindIII and NotI sites were filled in with Klenow. A 36 bp hypercleavable recognition site for PiSceI, which also contains a HindIII site, was inserted between EcoRI and SalI sites. Note that PiSceI is commercially available from New England Biolabs (Beverly, Mass.). Oligonucleotide ligation created AscI and PmeI sites between the SalI and HindIII sites. Thymidine kinase (TK), isolated from the knock-out vector pPNT (Tybulewicz et al., supra), was blunt-end ligated into a unique MscI site. Diagnostic digestion verified each unique restriction endonuclease recognition sequence site listed in FIG. 1D. A genomic fragment containing restriction endonuclease recognition sites listed in parentheses will, when cloned into the cognate unique site in this vector, destroy those genomic restriction endonuclease sites. For example, a SalI-digested fragment cloned into the XhoI site in the CWKO vector will destroy the XhoI site. Restriction endonucleases that are convenient for linearization of the completed knock-out gene targeting vector are boxed in FIG. 1D. Although other restriction endonucleases may be used to linearize the completed targeting vector, it will be understood that the site of the recognition sequence of the restriction endonuclease used to linearize the targeting vector should not be located in the promoter, coding sequence, or poly A signal associated with the targeted gene exon (or inserted transposon therein) or the thymidine kinase encoding sequences (including the promoter and poly A signal associated with the thymidine kinase-coding sequences).

Targeting of the Murine Neuroendocrine 7B2 Gene

In order to generate a diversity of biologically active peptides, mammals utilize endoproteolysis of biologically inactive polypeptide precursors. Recently, the prohormone convertase (PC) family of genes has been identified: these serine proteases are involved in the processing of polypeptide hormones such as insulin, glucagon, and proopiomelanocortin (reviewed in Seidah and Chretien, Trends Endicrinol. Metabol. 3: 133–140, 1992; Steiner et al., J. Biol. Chem. 267: 23435–23438, 1992). PC2, one of the PCs, interacts with neuroendocrine 7b2 in the secretory pathway (Braks and Martins, Cell 78: 263–273, 1994).

Figure 2A:
FIG. 2A is an agarose gel of PCR amplified DNA from amp/tmp-resistant colonies resulting from an in vitro transposition reaction.
Figure 2B:
FIG. 2B is the sequence of the transposition site (SEQ ID NO: 2) in the targeting vector, indicating that the transposition has taken place into mouse 7B2 exon 3.

We chose to use our transposon-based gene targeting approach to target the mouse neuroendocrine 7B2 gene. The 7B2 gene was found to be located within 50 kb of the 3' end of the formin gene (Wang et al., Genomics 39: 303–311, 1997). A 7.5 kb genomic SpeI fragment was isolated from a BAC (commercially available from Genome Systems, St. Louis, Mo.) and cloned into the XbaI site in the CWKO vector. A simple transposition reaction, entailing incubation and subsequent phenol extraction steps, was then performed according to the manufacturer's specifications (Perkin-Elmer Corp., Norwalk, Conn.), as before. Colony PCR reactions were performed using oligonucleotides homologous to exonic DNA. The primers used were 5'-AGTTTTCCCAAGAGGACAGG-3' (SEQ ID NO: 3) and 5'-TTCTTCCCACGCTGCAGGG-3' (SEQ ID NO: 4), which amplified exon 3 of the mouse 7b2 gene (Braks et al., Eur. J. Biochem 236: 60–67, 1996). The results of the colony PCR reaction indicated that 4 of 288 transposition events were marked by integration into the exon of interest. FIG. 2A shows a representative panel of colony PCR products. In clones in which a transposition event did not take place in the exon of interest, the endogenous 150 bp exonic band is present, thus indicating transposon integration had taken place elsewhere in the genomic clone. However, clones in which the transposition event did take place in the exon of interest showed the expected up-shift to 1.1 kb: in these clones, the transposon was inserted into exonic DNA. Such transposition events into the exon of interest (i.e., exon 3 of the mouse 7b2 gene) were labelled in FIG. 2A as 2–53 and 2–70 (note that the transposon is roughly 900 bp). Sequence data of a clone having a 1.1 kb PCR product, presented in FIG. 2B, confirmed that transposition had indeed taken place into exon 3 of the mouse 7B2 gene.

Our transposon-based gene targeting approach has been confirmed to be generally applicable by generating transpositions into exonic DNA of two other genomic fragments, which were used for the generation of gene targeting constructs. Since a number of transposition reactions may be performed in parallel, multiple constructs of different genes can be produced simultaneously using this procedure.

Homologous Recombination with the Transponson-mediated Knock-out Vector

Figure 3A:
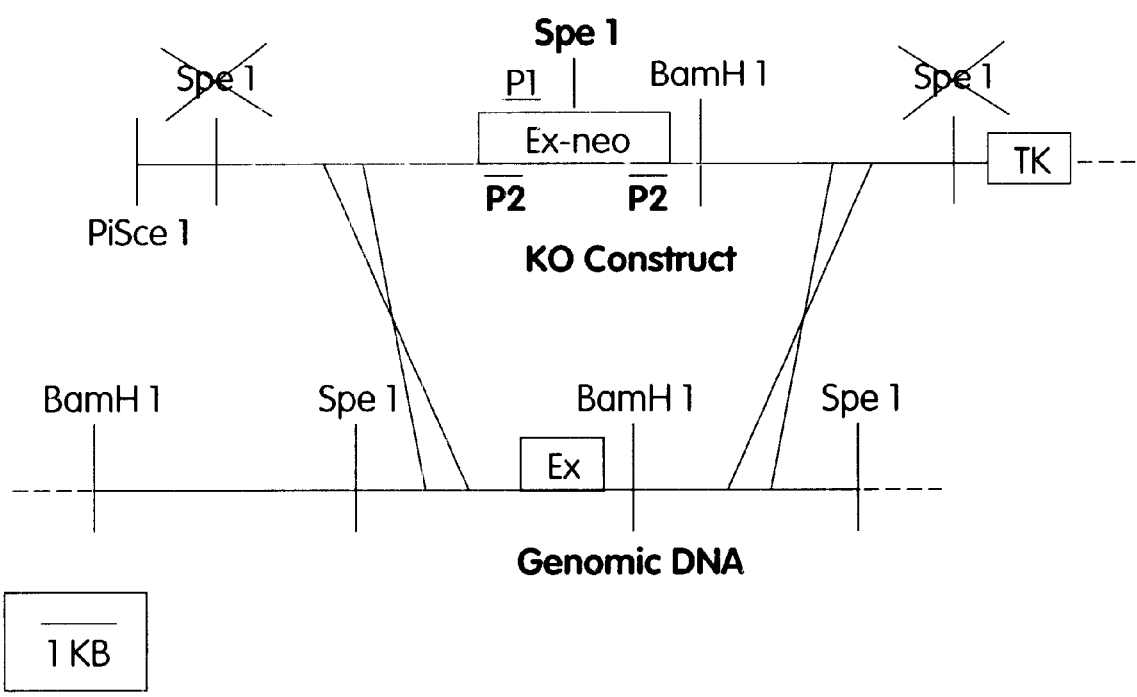
FIG. 3A is a schematic diagram representing a homologous recombination event between the targeting vector bearing the transposon-inserted 7B2 exon 3 DNA and genomic DNA, such that the external SpeI sites are reconstituted and a new SpeI site is added within the neo cassette.

As a final step, we transfected the 7b2 "knock-out" vector generated in the present study into embryonic stem cells, as described previously (Deng et al., Cell 82: 675–684, 1995). Briefly, 40 µg of linearized targeting vector was electroporated into embryonic stem (ES) cells and subjected to positive (G418) and negative (FIAU) selection. Resistant ES cell clones were isolated and expanded for genomic DNA isolation. This genomic DNA was subjected to subsequent analyses with Southern blotting analysis and other standard techniques (see, e.g., Ausubel et al., Current Protocols in Molecular Biology, John Wiley & Sons, New York, NY, 1994). Linearization of plasmids for transfection into embryonic stem cells was achieved by digestion of the hypercleavable site for PiSceI, which has a 36 base pair recognition site (Gimble and Wang, J. Mol. Biol. 263: 399–402, 1996) and has no reported recognition sites within the mouse genome. It is, of course, understood that while PiSceI is ideal to for gene targeting in mice, gene targeting in other animals (e.g., in pigs) is facilitated by use of a restriction endonuclease that has no or few recognition sites in the porcine genome. FIG. 3A is a schematic diagram showing that homologous recombination led to a restoration of the genomic SpeI sites which were originally destroyed in the targeting vector (by cloning the SpeI fragment into an XbaI site). Also shown on the schematic in FIG. 3A are genomic SpeI and BamHI sites, as well as an additional SpeI site within the neo cassette. The positions of transposon DNA (labelled P1) and exonic DNA (labelled P2) that were used as probes are also indicated in FIG. 3A.

Figure 3B:
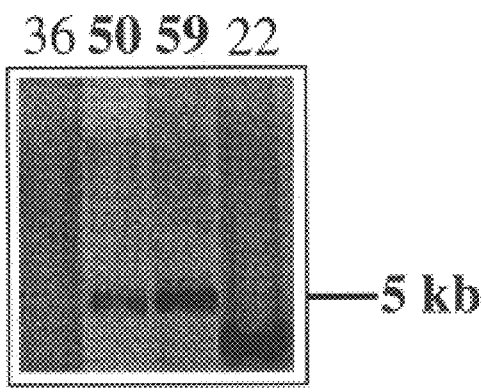
FIG. 3B is a Southern blotting analysis of genomic DNA digested with SpeI from four ES clones probed with labelled transposon DNA.
Figure 3C:
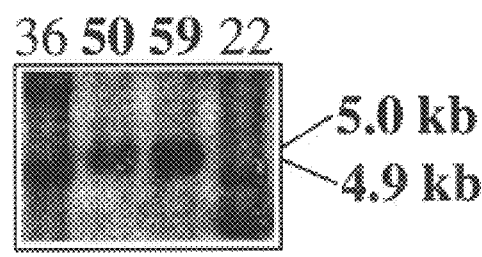
FIG. 3C is a Southern blotting analysis of genomic DNA digested with SpeI using exonic DNA from mouse neuroendocrine 7B2 as a probe.
Figure 3D:
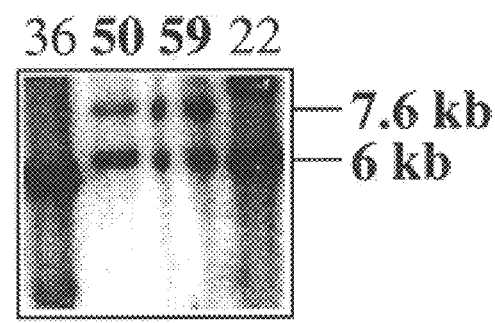
FIG. 3D is a Southern blotting analysis of genomic DNA digested with BamHI using exonic DNA from mouse neuroendocrine 7B2 as a probe.

Sixty-three G418-, FIAU-resistant ES clones were obtained, of which two were proven to have undergone homologous recombination. FIG. 3B shows that ES clones 50 and 59, which had undergone homologous recombination, had the predicted 5 kb band when using a transposon probe (listed as P1 in FIG. 3A). Two other clones did not undergo homologous recombination: ES clone 36 had no detectable band, and ES clone 22 had a band at 4 kb. FIG. 3C shows a genomic Southern blotting analysis using exonic DNA from mouse neuroendocrine 7B2 as a probe (listed as P2 in FIG. 3A). The probability of obtaining an insertional event which regained relatively rare-cutting enzyme sites at precisely the same location on both sides of the construct is extremely low. Since the neo cassette contained one SpeI site (see FIG. 3A), the predicted alteration in the genomic locus was a down-shift from 7.5 kb to a doublet at 5.0 kb and 4.9 kb in genomic SpeI digested DNA, which was seen in ES clones 50 and 59 in FIG. 3C (note that the neo cassette and the transposon make the final targeted locus 9.9 kb). This observation was confirmed in FIG. 3D, which shows a corresponding up-shift from 6 kb to 7.6 kb in a Southern blot of BamHI digested genomic DNA, using an alternate P2 probe. Note that both "knock-out" (7.6 kb) and endogenous (6 kb) bands were of equal intensity, indicating that the endogenous locus had been targeted.

Analysis of Probability of Homologous Recombination

Using the methods of the invention, the following simple example illustrates that, given sufficient numbers of random integration events, a number of desired integrants will almost certainly be isolated. In this example, assume that a given genomic clone is 7.5 kb and contains 375 bp of exonic sequences (genomic DNA is thought to contain roughly 5% exonic sequences). The chance of one random integration not occurring in the exonic DNA for this example will then be all non-exonic vector DNA divided by the total DNA, to the first power. Expressed mathematically, this is $((7.5\text{kb}+2.5\text{kb}-.375\text{kb})/(7.5\text{kb}+2.5\text{kb}))^1$, i.e., $(9,625/10,000)^1$, since the transposon may also insert in 2.5 kb of the knock-out vector which are not taken up by the ampicillin resistance cassette. The chance of 100 random integrations not occurring in the exonic DNA will by extension be $(9,625/10,000)^{100}$=2%. As described herein, 300 colony PCR reactions can be readily performed in under 2 hours, and the likelihood of not recovering a desired insert would then become $(9,625/10,000)^{300}$=0.001%. Thousands of transpositional events per reaction have been routinely obtained, so that the limiting factor is essentially the number of colony PCR reactions one chooses to perform.

Uses for Transposon-mediated Homologous Recombination

The transposon-mediated gene targeting approach of the invention may be generally applicable for the generation of insertional knock-out vectors. This technique is rapid, leading from genomic clone to finished construct in a minimum of 4 days, and a number of constructs may be generated simultaneously. In addition, different exons in the same genomic clone may be targeted. This can prove useful in proteins in which different truncations shed light on the functional significance of distinct protein domains. Finally, the generation of knock-in mice, traditionally an arduous task, is greatly simplified by the random integration of transposons bearing rare-cutting restriction endonuclease recognition sequences. Hence, with our technique, cloning any cDNA of interest in-frame into a specific genomic locus becomes much less challenging and time-consuming.

Transposons for Targeting Genes in Eukaryotic Cells

Certain selectable markers are capable of conveying drug resistance to both prokaryotic and eukaryotic selection drugs. However, the nucleic acid encoding the selectable marker must be operably linked to a promoter capable of directing expression in both prokaryotic and eukaryotic cells. Such a promoter may be created by fusing a eukaryotic promoter (e.g., the PGK promoter) with a prokaryotic promoter (e.g., a synthetic EM-7 E. coli promoter). For example, nucleic acid encoding the neo marker protein may be operably linked to the fusion promoter. A consensus poly A signal capable of terminating both prokaryotic and eukaryotic transcription may be positioned 3' to the nucleic acid encoding neo. Employment of a transposon incorporating this modified neo cassette will enable the propagation of transposon-integrated CWKO plasmids in bacteria grown in the presence of both ampicillin and kanamycin. Once a plasmid bearing a transposon insertion into a desired gene, or exon thereof, is identified, the plasmid may be directly linearized and used to homologously recombine eukaryotic cells, thereby bypassing the replacement of a prokaryotic selectable marker with a eukaryotic selectable marker. Resulting homologously recombined eukaryotic cells are resistant to both FIAU and G418.

Another gene capable of conferring drug resistance in both eukaryotic and prokaryotic cells is the Zeocin™ resistance gene which confers resistance to the drug, Zeocin™. The Zeocin™ drug and Zeocin™ resistance gene are both commercially available from Invitrogen (San Diego, Calif.). The Zeocin™ resistance gene cassette (nucleic acid encoding the the Zeocin™ resistance marker protein operably linked to a hybrid promoter that includes the eukaryotic CMV promoter and the bacterial synthetic EM-7 promoter) may be readily removed from the pZeoSV2 vector (Invitrogen, Carlsbad, Calif.) and subcloned into the transposon. Preferably, when the Zeocin™ resistance gene cassette is inserted into the transposon, it is flanked by rare cutting restriction endonuclease recognition sequences.

Eukaryotic Cells with One or More Targeted Genes

The utilization of the methods of the invention, as described, will greatly facilitate the generation of mice with targeted genes. Given the rapidity of the transposon-based generation of targeting vectors, it is understood that more than one vector can be produced at the same time. For example, the in vitro transposon reaction may be applied to a murine genomic library in the CWKO vector. Methods for the generation of such a library are well known in the art (see, for example, Ausubel et al., supra). Murine genomic DNA is also commercially available (from, e.g., Clontech Laboratories Inc., Palo Alto, Calif.), and may be readily prepared for insertion into the CWKO vector. Following integration of the transposons, bacterial colonies may be subjected to PCR colony screening using primers specific for all desired targeted genes; For example, the bacterial colonies may first be screened for transposon insertion into the mouse neuroendocrine 7B2 gene. Following identification of colonies which have targeted 7B2, the remaining colonies may next be screened for transposon insertion into a second gene, e.g., actin. Following identification of actin-targeted colonies, the remaining colonies may be screened for transposon insertion into yet another gene of interest. Since bacteria colony containing plates are easily duplicated, a genomic library carrying transposon insertions may be maintained indefinitely in bacteria (with appropriate passaging of colonies onto fresh AMP/TMP plates) for future screens for targeted genes of interest. Likewise, the plasmid DNA from these bacteria may be isolated by standard maxi-prep techniques, and re-transformed into bacteria for expansion when a future screen is desired.

Once a transposon insertion event into a targeted gene is identified, a eukaryotic selectable marker is inserted into rare-cutting restriction endonuclease recognition sites located on the transposon inserted into the gene of interest, or an exon thereof. The sites preferably flank the dhfr prokaryotic selectable marker gene. It is understood that any eukaryotic selectable marker may be utilized (e.g., hygB, pac, hisD, neo). For example, an exon from the murine neuroendocrine 7B2 gene may be inserted with neo, while an exon from the murine actin gene may be inserted with pac. The targeting vector is then linearized and used to homologously recombine with chromosomal DNA in eukaryotic cells (e.g., murine ES cells), which are then treated with FIAU and the drug corresponding to the transposon-inserted eukaryotic marker. It will be understood that linearized vectors may be from different targeting vectors; however the two vectors preferably bear exons inserted with two different eukaryotic selectable markers. For example, both the neo-inserted neuroendocrine 7B2 gene and the pac-inserted actin gene may be targeted in the same murine ES cell. The ES cells are then subjected to selection in FIAU, G418, and puromycin.

It is understood that this simultaneous targeting of more than one gene may be utilized for the development of "knock-out mice" (i.e., mice lacking the expression of a targeted gene product), "knock-in mice" (i.e., mice expressing a fusion protein or a protein encoded by a gene exogenous to the targeted locus), or mice with a targeted gene such that a truncated gene product is expressed.

Although the use of a genomic library does not allow the destruction of a restriction endonuclease recognition site flanking the targeted gene exon, homologous recombination events in ES cells may be screened for by Southern blot alone without the additional screen for restoration of the destroyed restriction endonuclease recognition site. Should more than one gene be targeted, Southern blot analysis with probes from both genes may be utilized. If the genes are of detectably different sizes, both probes may be used at the same time.

Eukaryotic Cells with a Targeted Gene which Partially Encodes a Fusion Protein

Cells and rodents expressing fusion proteins of proteins tagged with lacZ or GFP (green fluorescent protein) have been utilized for precise developmental expression studies (LeMouellic et al., Proc. Natl. Acad. Sci. USA 87: 4712–4716, 1990; Mansour et al., Proc. Natl. Acad. Sci. USA 87: 7688–7692, 1990; Sosa-Pineda et al., Nature 386: 399–402, 1997). In addition, fusion proteins of targeted gene products fused to an oncogene have been used as a model for human cancer translocations (Corral et al., Cell 85: 853–861, 1996; Castilla et al., Cell 87: 687–696, 1996; Yergeau et al., Nature Gen. 15: 303–306, 1997). Utilization of the methods of the invention will greatly facilitate the construction of such transgenic cells and animals. For example, an exogenous gene, encoding, e.g., lacZ, may be fused to a targeted gene at the carboxy terminus of the targeted gene product by subcloning an exon into the CWKO vector. Following identification of a transposon insertion into the exon by the methods described herein, the dhfr gene on the transposon may be replaced with nucleic acid from a desired exogenous gene (e.g., lacZ or an oncogene) separated from the nucleic acid encoding a eukaryotic selectable marker (e.g., the PGK neo$^c$ bpA neo cassette) with a stop codon such that the inserted nucleic acid from the desired exogenous gene is in frame with and adjacent to the exon. The inserted nucleic acid encoding a eukaryotic selectable marker is, thus, located at the extreme carboxy-terminal end of the fusion protein. It is understood that should the exogenous gene be fused to the targeted gene at the amino terminus of the targeted gene, the heterologous DNA inserted into the transposon integrated into the targeted exon includes the entire neo cassette located 5' to a promoter operably linked to the exogenous gene of choice. The exogenous gene is inserted into the transposon such that it is in frame with and 5' adjacent to the exon of the targeted gene. The targeting vector is next homologously recombined into eukaryotic cells. Genomic DNA of FIAU and G418 resistant clones may then be screened for restoration of the destroyed restriction endonuclease sites on the exon and by Southern blot analysis with a probe corresponding to exonic DNA.

Eukaryotic Cells with a Targeted Gene Encoding a Truncated Protein

Cells expressing truncated proteins are useful in analysing the roles of specific domains of proteins in the biological functions of the full length proteins. For example, should the targeted gene produce a product whose two functional domains are separated by the amino acid residues encoded by the fourth exon, the fourth exon may be subcloned into the CWKO vector and subjected to an in vitro transposition reaction. Once a transposon has inserted into exon 4, the dhfr gene on the transposon may be replaced with a eukaryotic selectable marker cassette (e.g., PGK neo$^c$ bpA) plus addition sequences. For a C-terminal truncated targeted gene product, the selectable marker cassette bears additional sequences 5' to the PGK promoter. These 5' sequences include stop codons in all three frames, followed by a poly A signal, such that exon 4 transcription terminates prior to the initiation of transcription of the selectable marker cassette. Should a N-terminal truncated targeted gene product be desired, the additional sequences are 3' to the selectable marker cassette and include a promoter operably linked to an initiator codon that is in frame with exon 4 such that the truncated protein is expressed from DNA (i.e., exon 4) located 3' to the transposon insertion site. A cell bearing the truncated protein may then be detected by the restoration of the destroyed restriction endonuclease sites flanking exon 4, and by Southern blot analysis using exon 4 DNA as a probe.

Eukaryotic Cells with Nucleic Acid Encoding a Protein Introduced into the Locus of a Targeted Gene Several recent papers have indicated the power of "knock-in" technology in analyses of the functional complementation between related genes (Hanks et al., Science 269: 679–682, 1995). The methods of the present invention will greatly facilitate the rapidity with which these mice may be generated. Generation of "knock-in" cells and mice is accomplished by designing a targeting vector in which the prokaryotic selectable marker gene (e.g., dhfr) located on the transposon is replaced with nucleic acid (e.g., genomic DNA or, more preferably, cDNA) encoding a second protein together with a eukaryotic selectable marker cassette. Homologous recombination of this targeting vector with the chromosomal DNA in eukaryotic cells (preferably, ES cells) is accomplished by screening genomic DNA for restoration of destroyed restriction endonuclease recognition sequences flanking the targeted exon and by Southern blot analysis with probes corresponding to the targeted exon.

Utilization of Eukaryotic Cells with Targeted Genes

A eukaryotic cell with one or more targeted genes allows the analysis of the effects of the targeted gene in the cell. For example, a terminally differentiated CD8$^+$ T cell may have a targeted disruption of the lck gene, such that no 1ck protein is expressed. Although the targeted gene is present on only one chromosome, lack of 1ck expression may be accomplished nevertheless, since most terminally differentiated cells are functionally hemizygous. This cell may be used for the functional analysis of antigen responsiveness in the absence of 1ck, and to determine if other endogenous protein tyrosine kinases can compensate for the lack of 1ck. Similarly, this cell may express a fusion protein of 1ck fused to the fluorescent marker, green fluorescent protein (GFP). The subcellular localization of the 1ck protein may then be assessed during the various biological responses of the protein.

A murine ES cell bearing targeted gene(s) may be used to generate heterozygous and homozygous mice using standard techniques (Tybulewicz et al., supra; Capecchi, supra). Hence, depending upon the type of disruption in the targeted gene, mice with no expression of the targeted gene, expression of a fusion protein partially encoded by the targeted gene, or expression of a different gene product from the targeted gene locus may be generated. Analysis of the effects on the disrupted targeted genes may then be assessed on an organismal level. In addition, murine embryonic fibroblast cells (MEFs) may be derived from murine ES cells or transgenic mice according to standard procedures (Deng et al., Cell 82: 675–684, 1995), and may allow more detailed studies in cell culture.

7b2 Knock-out Mice

After electroporation of the 7b2 gene-targeting construct into embryonic stem (ES) cells, several ES clones were shown to have undergone homologous recombination. Two of these were injected into blastocysts, chimeric mice were derived, and germline transmission was shown to occur. We then mated the chimeric mice to 129Svev strain females to place the targeted 7b2 gene on a pure genetic background. All of our 7b2 null mice were derived from these two independent ES clones; however, no difference was noticed between the two independent mouse lines.

Figure 4A:
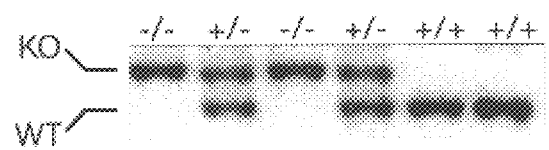
FIG. 4A is a Southern blotting analysis showing the genotype of mice that were 7b2–/–, 7b2+/–, and 7b2+/+.
Figure 4B:
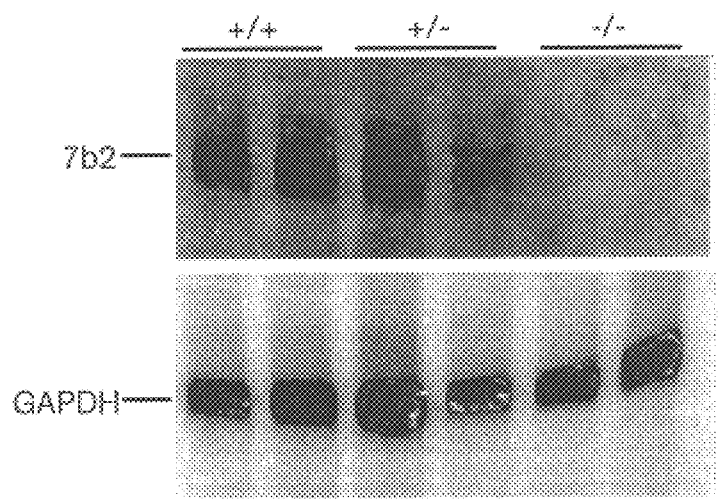
FIG. 4B is a Northern blotting analysis showing that 7b2–/– mice were null (i.e., showed no expression) for 7b2 RNA, while 7b2+/+ and 7b2+/– mice did express 7b2 RNA. Equal loading of all lanes is shown by comparable expression of GAPDH RNA.

Genotyping of heterozygotic matings indicated offspring of all possible genotypes (see FIG. 4A). In order to analyze 7b2 RNA levels, total RNA was extracted from whole brains of 7b2+/+ and 7b2-/- mice, and subjected to Northern blotting analysis using the 7b2 exon 2 DNA as a probe according to standard techniques (see, e.g., Ausubel et al., supra). As shown in FIG. 4B, 7b2 null mice were found to lack detectable 7b2 RNA transcripts.

Figure 4C:
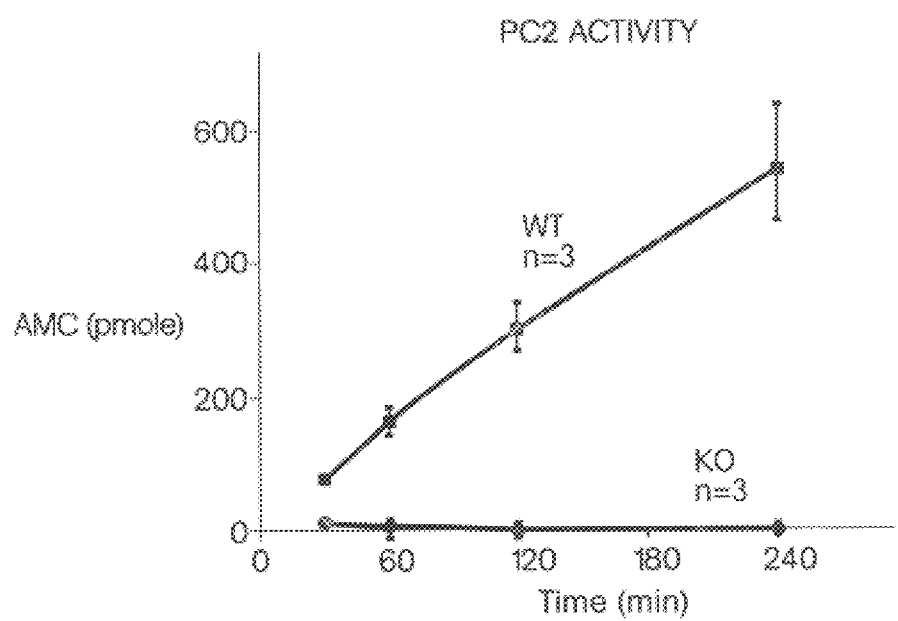
FIG. 4C is a graph showing the comparison of the activity of PC2 isolated from brains of three wild type (i.e., 7b2+/+) and three 7b2 null (i.e., 7b2−/−) mice. There was a complete absence of PC2 activity in the brains of 7b2 null mice.

Several studies have indicated that PC2 activity might be dependent upon 7b2 function (Braks and Martens Cell 78: 263–273, 1994; Braks and Martens, FEBS Lett. 371: 154–158, 1995; Braks et al., Eur. J. Biochem. 238: 505–510, 1996; Zhu et al., J. Biol. Chem. 271: 23582–23587, 1996; Zhu et al., Proc. Natl. Acad. Sci. USA 93: 4919–4924, 1996). Hence, whole protein was extracted from wild type and 7b2 null mouse brains, PC2 protein was immunopurified with anti-PC2 polyclonal antibody, and fluorometric PC2 activity assays were performed. The PC2 activity assays were performed by standard procedures (see, e.g., Lindberg et al., Biochemistry 34: 5486–5493, 1995; Zhu et al., J. Biol. Chem. 271: 23582–23587, 1996, herein incorporated by reference). Briefly, mouse brains were homogenized in a non-denaturing detergent (e.g., not SDS) and TBS. After centrifugation to obtain soluble proteins, PC2 antibody was added (pre-bound to Protein A beads). This mixture was incubated for 4 hours at 4° C. The beads were thereupon pelleted by centrifugation and washed in TBST. A fluorometric assay based upon PC2-mediated liberation of amimomethylcoumarin (AMC) was then performed using the fluorogenic substrate, pGlu-Arg-Thr-Lys-Arg-AMC (commercialy available from Peptides International, Lexington, Ky.), as previously described (Zhu and Lindberg, J. Cell. Biol. 129: 1641–1650, 1995, herein incorporated by reference). Note that a fluorescent standard AMC (commercially available from Peninsula Laboratories Inc., Belmont, Calif.) was used to calibrate the fluorometer. A comparison of the results obtained with proteins from wild-type and 7b2 null mice is shown in FIG. 4C. As shown, 7b2-/- mice completely lack PC2 activity (FIG. 4C), thus proving that PC2 activity is dependent upon 7b2.

Figure 5A:
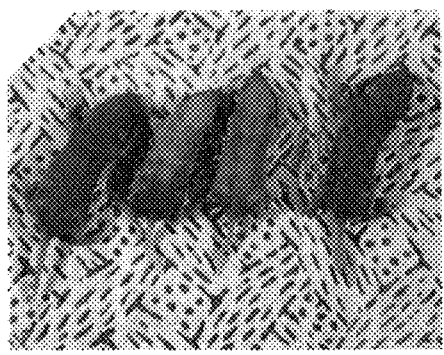
FIG. 5A is a photograph showing two four day old 7b2 null mice (in center) flanked by two four day old wild-type mice. The 7b2 null mice were pale and showed significant bruising.
Figure 5B:
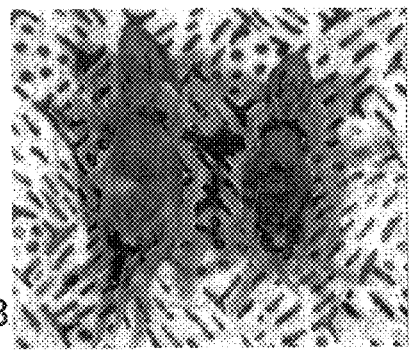
FIG. 5B is a photograph showing a four day old 7b2 null mouse (at right) with a four day old wild-type mouse (at left). 7b2 null mice had significant bleeding into the peritoneum.
Figure 5C:
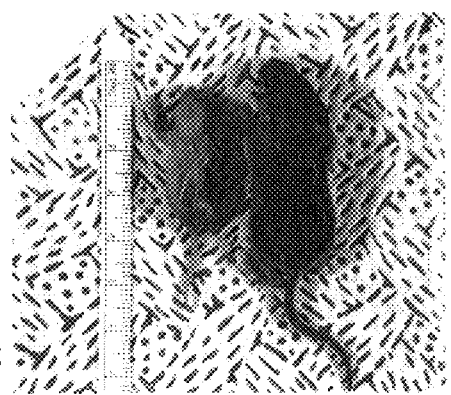
FIG. 5C is a photograph showing a twelve day old 7b2 null mouse (at left) with a twelve day old wild-type mouse (at right). Note the significant runting and parchment-like skin in the twelve day old 7b2 null mouse as compared to the wild-type mouse.
Figure 5D:
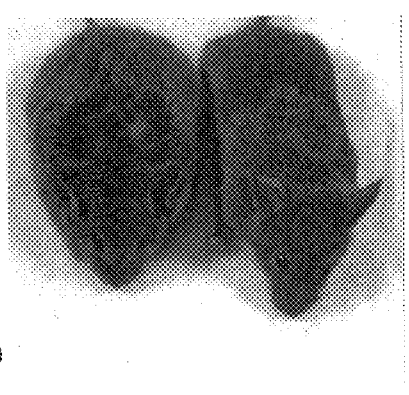
FIG. 5D is a photograph showing a six week old 7b2 null mouse (at left) with a six week old wild-type mouse (at right). Note the marked obesity (e.g., the prominent fat depositions on the back and around the neck) in the six week old 7b2 null mouse as compared to the wild-type mouse.

At four days of age, 7b2 null mice (two are shown in the middle of FIG. 5A; two wild type mice are flanking them)

were observed to be pale and ecchymotic (note especially the severe bruising of the left 7b2 knock-out mouse). Many 7b2 null mice suffered from significant bleeding into the abdomen (see prototypical four day old wild type mouse on the left versus null mouse on the right, FIG. 5B). Only 11% of 7b2 null mice survived to weaning, and 7b2 null mice were often very severely runted, with parchment-like skin (null versus wild type mice are shown at 12 days of age, FIG. 5C). Despite this significant runting, however, those 7b2 null mice which did survive weaning actually became obese after weaning, with a prominent fat deposition on the back and around the neck (six week old 7b2 null and wild type mice are shown in FIG. 5D).

Figure 6A:
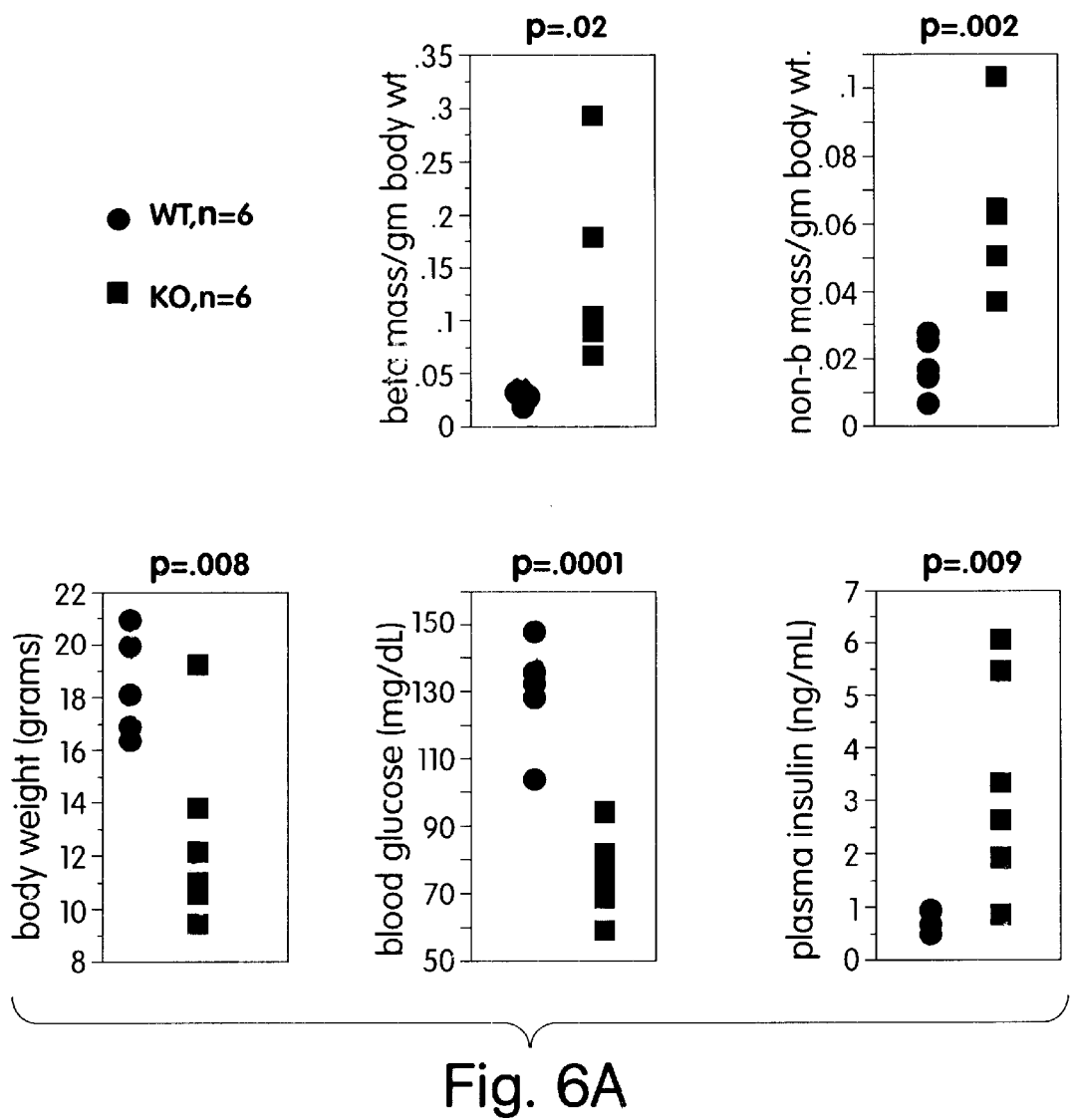
FIG. 6A is a series of graphs showing the differences in various metabolic parameters observed between 7b2 null mice (depicted as squares on the right of each graph) and wild-type mice (depicted as circles on the left of each graph). 7b2 null mice had a higher ratio of pancreatic beta cell islet mass/total body weight as compared to wild-type mice (p=0.02) and had a higher ratio of pancreatic non-beta cell islet mass/total body weight (p=0.002), thus reflecting generalized islet cell hyperplasia in 7b2 null mice. Furthermore, 7b2 null mice were runted (i.e., had a lower body weight than wild-type mice, p=0.008), were hypoglycemic (i.e., had lower blood glucose levels as compared to wild-type mice, p=0.0001), and were hyperinsulinemic (i.e., had higher levels of plasma insulin as compared to wild-type mice, p=0.009).

One observation of the 7b2 null mice was that the animals appeared to be suffering from metabolic disturbances. Therefore, we next analyzed several metabolic parameters. As shown in FIG. 6A, pancreatic beta and non-beta islet mass was significantly expanded in 7b2-/- mice. Furthermore, 7b2 null mice were severely hypoglycemic and hyperinsulinemic, as determined by the lower blood glucose levels and elevated serum insulin levels, respectively, seen in 7b2 null mice as compared to wild-type mice. For these analyses, 4–5 week old mice were weighed, and blood was analyzed using a standard glucometer. Plasma insulin was measured by radioimmunoassay, and islet mass determinations were performed by morphometric analysis.

Figure 6B:
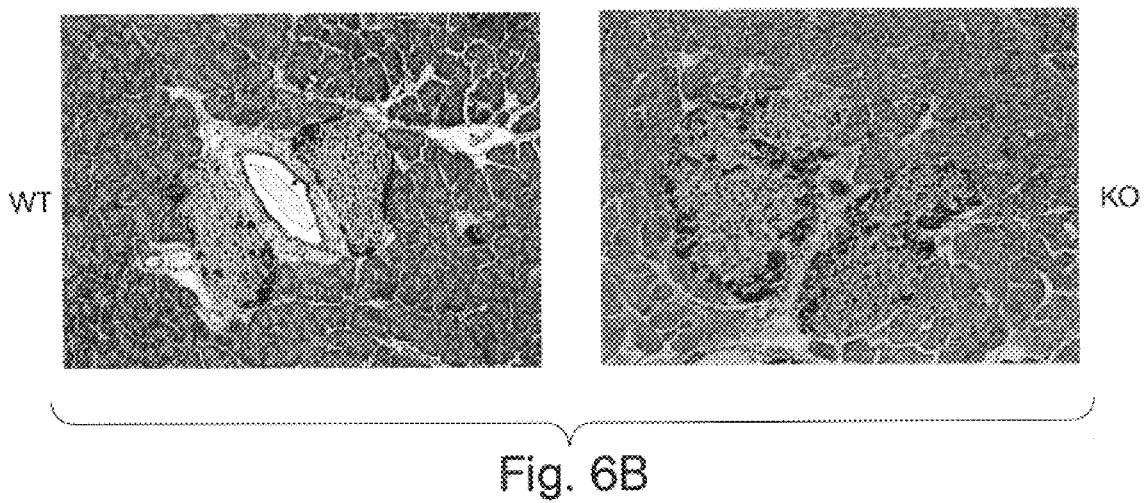
FIG. 6B are two photographs (20×) showing the pancreatic pathology in five week old wild-type (left) and 7b2 null (right) mice. 7b2 null mice showed islet hyperplasia and abnormal islet morphology.

The metabolic disturbances observed in the 7b2 null mice were accompanied by morphological effects on the pancreas. Mouse tissue (e.g., pancreas) was removed and fixed in Optimal Fix (American Histology Reagent, Lodi, Calif.), blocked in paraffin, sectioned at 10 μm, and stained with hematoxylin and eosin, according to standard techniques. FIG. 6B shows photographs at 20× magnification of representative pancreas specimens from 7b2 null (KO) and wild-type (WT) mice at five weeks of age, indicating both the increased size and markedly abnormal morphology of islets in the pancreas of 7b2 null mice. Hence, the 7b2 null mouse, the first knock-out mouse produced using a transposon-based technique, was found to lack PC2 activity, indicating that PC2 activity is dependent upon 7b2 function. The 7b2 null mouse was found to be hypoglycemic and hyperinsulinemic, with generalized islet cell expansion and altered islet morphology.

7b2 Null Mice have Cushing's Disease

In order to gain a better understanding of the severe phenotype associated with loss of 7b2, further histological analyses were performed on 7b2 null mice, as described above. 7b2 null skin (FIG. 7B, 20×) showed marked thinning and hyperkeratosis of the epidermis, as well as dermal atrophy when compared to wild type skin (FIG. 7A, 20×). Even more strikingly, 7b2-/-liver was markedly pathological, with destruction of the normal lobular liver architecture and severe fat vacuolation (see FIG. 7D for null as compared to FIG. 7C for wild type, both at 20×magnification). Finally, 7b2 null spleens were roughly one-fifth the size of wild type spleen, and showed a loss of normal architecture and a generalized a myeloid immaturity (see FIG. 7F null versus FIG. 7E wild type, 5×magnification for both).

Given the surprising finding of abnormal fat deposition; epidermal thinning and ecchymoses; bleeding diathesis; splenic myeloid depletion; and fat vacuolation of the liver in 7b2 null mice, we next analyzed whether the 7b2 mice suffered from hypercortisolism.

Hypersecretion of cortisol by the adrenal cortex (or over production of other similar steroid hormones, such as hydrocortisone, prednisone, methyl-prednisolone, or dexamethasone) causes a complex of hormonal effects called Cushing's disease, which is sometimes referred to as Cushing's syndrome. Cushing's disease can result from a general hyperplasia of one of both adrenal cortices which may, in turn, be caused by increased secretion of ACTH by the anterior pituitary.

Figure 8A:
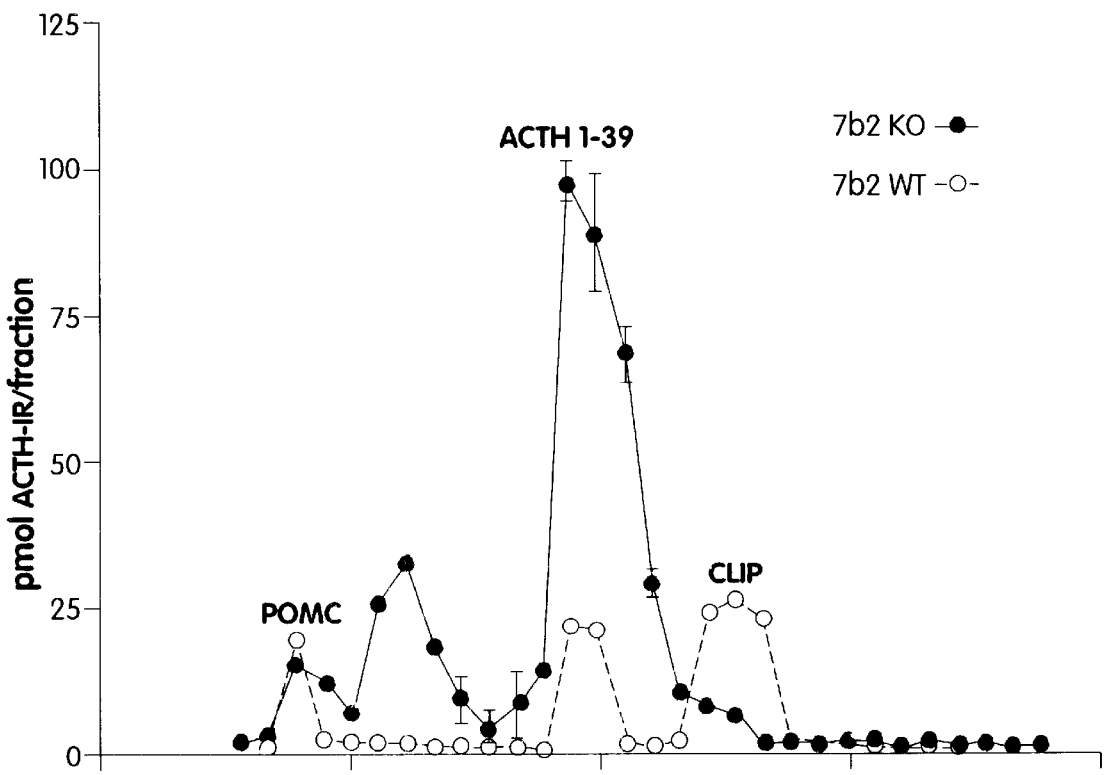
FIG. 8A is a graph showing the increased level of ACTH in the pituitary of 7b2 null mice (solid line, filled circle) as compared to wild-type mice (dotted line, open circle).

Analysis of the pituitary intermediate lobe in our 7b2 mice revealed that this lobe was indeed significantly enlarged in 7b2 null mice as compared to wild-type mice. Furthermore, pituitary ACTH was found to be markedly elevated in 7b2 null mouse (FIG. 8A). To measure ACTH, pituitaries from 7b2 null mice or from wild-type control mice were homogenized in ice cold 1N acetic acid by sonication. The homogenates were then collected in a microcentrifuge tube and centrifuged for 5 minutes in a microcentrifuge. The aliquots were then injected into a high pressure gel permeation chromatography and run in 32% acetonitrile plus 0.1% trifluoroacetic acid. Fractions were then assayed using ACTH-IR peptides directed against residues 11–17 of ACTH.

Figure 8B:
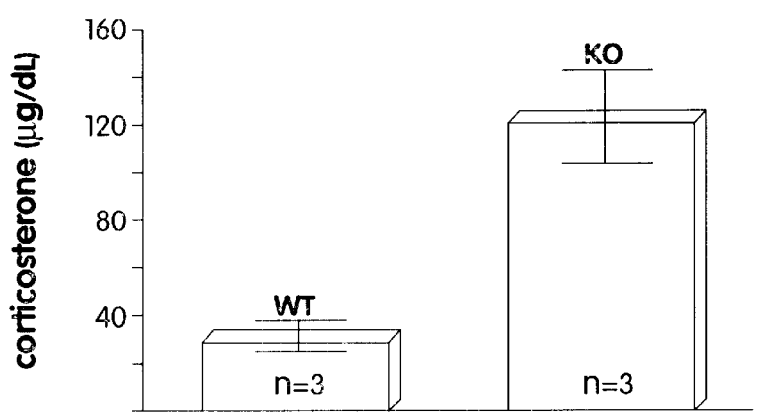
FIG. 8B is a graph showing the higher concentration of corticosterone seen in the sera of 7b2 null (KO) as compared to wild-type (WT) mice.
Figure 8C:
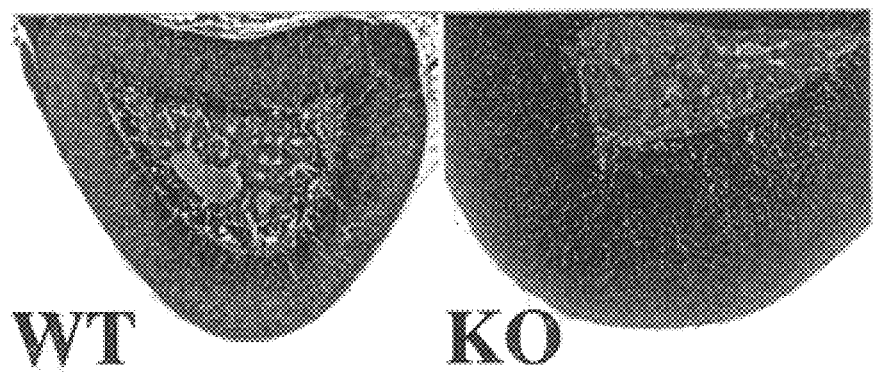
FIG. 8C is a pair of photographs (20×) showing the adrenal cortex in wild-type (left) and 7b2 null (right) mice. Note the markedly expanded adrenal cortex in the 7b2 null mouse as compared to wild-type.

We next looked at the serum levels of corticosterone in 7b2 null versus wild-type mice. Corticosterone levels in mice are a reflection of cortisol levels in humans since mice produce corticosterone instead of cortisol. Corticosterone assays were performed on serum as described previously (Meiner et al., Proc. Natl. Acad. Sci. USA 93: 14041–14046, 1996). The serum corticosterone levels in 7b2 null mice were found to be roughly four-fold higher than the levels seen in wild-type mice (FIG. 8B). Finally, the adrenal cortex was greatly expanded in 7b2 null mice (as seen by histological analysis in FIG. 8C).

Figure 8D:
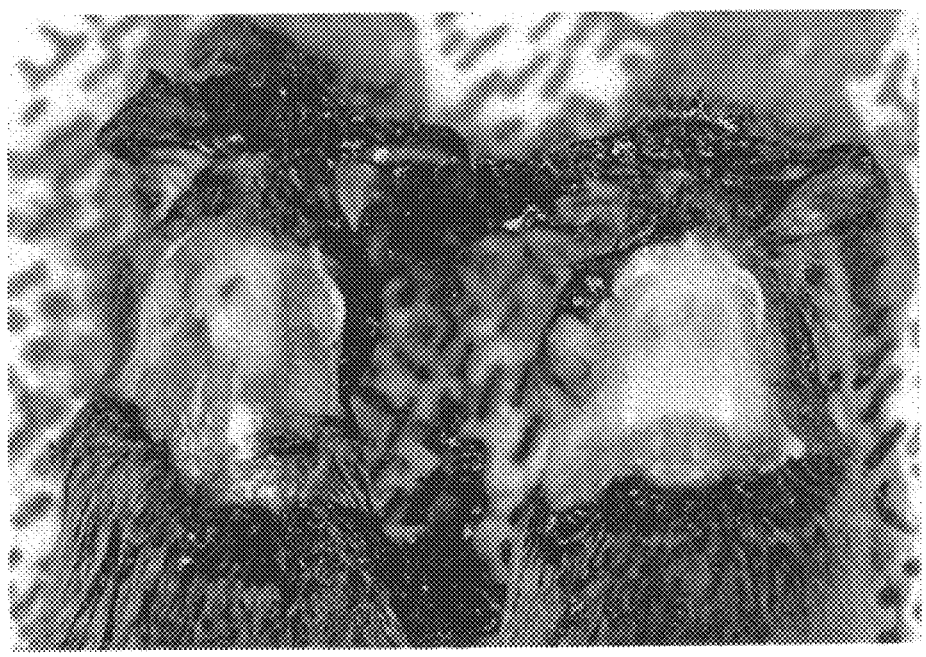
FIG. 8D is a pair of photographs showing the characteristic "buffalo hump" fat deposit seen on 7b2 null mice (right) that was missing on wild-type control mice (left).

Another characteristic of Cushing's disease is the mobilization of fat from the lower part of the body, with concomitant extra deposition of fat in the thoracic and upper abdominal regions, giving rise to a so-called "buffalo hump." As final confirmation that 7b2 null mice indeed had Cushing's disease, all of the 7b2 null mice surviving past four weeks of age showed a characteristic "buffalo hump" fat deposition on the back (see FIG. 8D). Hence, we have found that 7b2 null mice unexpectedly developed Cushing's disease, with a multiple sequelae of hypercortisolism, thus uncovering a previously unknown role for 7b2 in the control of steroidogenesis.

Our discovery that 7b2 null mice developed pituitary Cushing's disease, and succumbed to the sequelae of hypercortisolism, is surprising. Cushing's disease, or hyperadrenocorticism, is caused by an excess of cortisol in the body. Our unexpected results indicated that 7b2 appears to have PC2-independent effects on steroidogenesis, perhaps via control of the processing of proopiomelanocortin (POMC), the precursor polypeptide whose cleavage results in the production of ACTH. For example, 7b2 may interact with an as-yet undiscovered prohormone convertase that is involved in POMC processing. Thus, our findings allow detailed characterization of 7b2 control of steroidogenesis, either direct or indirect, which is important for a proper understanding of both normal human physiology, as well as hypercortisolic disease states (e.g., Cushing's disease), hypocortisolic disease states (e.g., Addison's disease), hypoglycemia, and hyperglycemia (e.g., diabetes).

The Role of 7b2 in Endocrine Disorders

Our unexpected finding that 7b2 null mice have Cushing's disease allows for the development of methods and reagents to treat or diagnosis patients having (or suspected of having) endocrine disorders. Any cell, tissue, or product of the 7b2 null mouse (or the mouse itself) which lacks 7b2 RNA or 7b2 protein may be used as a model for understanding endocrine mechanisms.

For instance, these mice are useful for developing methods and reagents for treating or diagnosing patients having, or suspected of having, a hypercortisolism disorder such as Cushing's disease, or a hypoglycemic disorder. Furthermore, these mice may find use in the development of methods and reagents to treat or diagnosis patients having (or suspected of having) a hypocortisolism disorders, such as Addison's disease, or a hyperglycemic disorder. In accordance with the teachings of the invention, the sequence of the human 7b2 gene and protein (Braks et al., Eur. J. Biochem. 236: 60–67, 1996; Martens, G. J., FEBS Lett. 234: 160–164, 1988) may be thus manipulated to provide therapeutic reagents and methods for patients suffering from an endocrine disorder.

The 7b2 null mouse provides an excellent non-human test subject for live-animal screens of any compound (including those compounds isolated using the methods described below) suspected of being useful as a therapeutic to treat or alleviate symptoms in patients suffering from endocrine disorders such as hypercortisolism disorders (e.g., Cushing's disease), hypocortisolism disorders (e.g., Addison's disease), hypoglycemia, or hyperglycemia (e.g., diabetes). A therapeutic compound for use in patients having (or suspected of having) a hypercortisolism disorder will alleviate at least one, and preferably at least two, of the symptoms of these mice. Hence, a compound that can treat or alleviate the disease symptoms of hypercortisolism disorder, when administered to a 7b2 null mouse, will lead to at least one of the following: a restoration of normal PC2 activity; a reduction in runting; a restoration of normal skin coloring and a reduction in bruising; a reduction in bleeding into the peritoneum; a reduction of the "buffalo hump;" a reduction in obesity; a restoration of normal pancreatic islet cell mass; a restoration of normal blood glucose levels; a restoration of normal plasma insulin levels; a restoration of a morphologically normal liver; a restoration of a morphologically normal spleen; a restoration of a normal level of ACTH; a restoration of a normal serum concentration of corticosterone; and a restoration of a morphologically normal adrenal cortex.

Alternatively, a compound that can treat or alleviate the disease symptoms of a hypocortisolism disorder may, when administered to a 7b2 null mouse, lead to the exacerbation of one or more of the abnormalities seen in the mouse. In addition, a compound that is found to lower blood glucose levels (for treatment of patients with hyperglycemia) may actually kill a 7b2 null mouse due to a further lowering of the already-reduced blood glucose levels in 7b2 null mice. Likewise, a compound that is found to increase blood glucose levels (for treatment of patients with hyperglycemia) may restore to a 7b2 null mouse normal blood glucose levels.

Diagnostic Methods for Endocrine Disorders

For diagnostic methods, a patient suspected of having or developing an endocrine disorder, such as hypocortisolism, hypercortisolism, hypoglycemia, or hyperglycemia, may be tested for the level of expression (or the level of activity) of the neuroendocrine 7B2 gene. The 7b2 expression level may be measured at the protein or RNA level, and may be deemed to be normal or abnormal (e.g., reduced or increased) by comparison to the level of a control individual. 7b2 activity level may be measured, for example, by the ability of the protein to interact with PC2.

For example, a patient suspected of having or developing an endocrine disorder may be tested for a abnormal plasma level of 7b2 as compared to the plasma level of 7b2 in a healthy, age-matched, gender-matched control individual. Protein levels of 7b2 may be readily assayed in plasma and cerebral spinal fluid, although the 7b2 protein (and RNA) may also be collected from, for example, the anterior pituitary lobe and the thyroid gland. A reduction in the level of 7b2 protein or RNA is an indication that the patient either has a hypercortisolism disorder, such as Cushing's disease, or a hypoglycemic disorder, or has a predisposition to develop a hypercortisolism disorder or a hypoglycemic disorder. Conversely, an increase in the level of 7b2 protein or RNA is an indication that the patient either has a hypocortisolism disorder, such as Addison's disease, or a hyperglycemic disorder, or has a predisposition to develop a hypocortisolism disorder or a hyperglycemic disorder.

Likewise, a patient suspected of having (or with a predisposition to develop) an endocrine disorder may be assessed for a reduction (in the case of hypercortisolism or hypoglycemia) or an increase (in the case of hypocortisolism or hyperglycemia) in 7b2 activity. 7b2 protein may be collected from the patient and a healthy age-matched, gender-matched control individual, and compared for activity, such as an ability to be secreted, and an ability to interact with PC2.

A patient suspected of having or developing an endocrine disorder may also be screened for a mutation in the gene encoding the 7b2 protein. The mutation can be detected by analyzing genomic DNA, RNA, or mRNA, collected from any tissue. In one example, white blood cells are collected from an individual and genomic DNA subjected to Southern blotting analysis for the loss (or gain) of a restriction endonuclease recognition site that is different from a 7b2 gene from a healthy, preferably racially-matched individual. The presence of a mutation (i.e., the loss or gain of a restriction endonuclease site within the 7b2 gene) is an indication that the patient has an endocrine disorder, or has a predisposition to develop an endocrine disorder. If the mutation results in a reduction in the amount or activity of the 7b2 protein, the patient may have, or be predisposed to develop, a hypercortisolism disorder, such as Cushing's disease, or a hypoglycemic disorder. Alternatively, if the mutation results in an increase in the amount or activity of the 7b2 protein, the patient may have, or be predisposed to develop, a hypocortisolism disorder, such as Addison's disease, or a hyperglycemic disorder. Such a diagnosis can be confirmed with an analysis of the patient's plasma level of 7b2 protein.

Additionally, a mutation in a 7b2 gene in a patient suspected of having or developing an endocrine disorder may be detected by sequencing the patient's 7b2 gene or an RNA product thereof. Genomic material may be collected from any nucleated cell, whereas RNA may be collected from any cell tissue (e.g., pituitary tissue) that produces the 7b2 protein. Nucleic acid sequence analysis may be performed according to any standard procedure (see, e.g., Ausubel et al., supra) or at a sequencing facility, and compared to the 7b2 gene or RNA sequence of a healthy, preferably racially-matched individual. The presence of a mutation is an indication that the patient has or is likely to develop an endocrine disorder. A mutation resulting in a reduction in the amount or activity of the 7b2 protein is an indication that the patient may have, or may be predisposed to develop, a hypercortisolism disorder, such as Cushing's disease, or a hypoglycemic disorder. A mutation that results in an increase in the amount or activity of the 7b2 protein is an indication that the patient may have, or may be predisposed to develop, a hypocortisolism disorder, such as Addison's disease, or a hyperglycemic disorder. Such a diagnosis can be confirmed subsequently or concurrently with an analysis of the patient's plasma level of 7b2 protein.

Methods and Reagents for Treating an Endocrine Disorder

For a patient suffering from an endocrine disorder, our discovery allows for the development of reagents that may alleviate the disease symptoms. It will be understood that such a patient may or may not show an altered (i.e., abnormal) level of 7b2 protein expression or activity.

(a) Methods and Reagents for Treating Hypercortisolism and Hypoglycemia

7b2 protein, or DNA encoding the 7b2 protein (e.g., the 7b2 gene), may be administered to neuroendocrine cells or pituitary cells in patients suffering from a hypercortisolism disorder such as Cushing's disease, or patients suffering from hypoglycemia Similarly, a compound that increases the level of expression of 7b2 may be administered to patients with a hypercortisolism disorder or with hypoglycemia. Such a compound may activate transcription of the 7b2 gene, and may be isolated using the promoter of the human 7b2 gene. For example, the promoter of the human 7b2 gene (GenBank Accession No. X94303; Braks et al., Eur. J. Biochem. 236: 60–67, 1996) may be operably linked to DNA encoding a reporter protein (e.g., GFP, luciferase, and lacZ) and used to transfect a cell line, such as COS cells. Pools of compounds, nucleic acids (e.g., a cDNA library), or proteins may then be screened for an ability to activate the expression of the reporter gene. In an assay of a mixture of compounds where GFP is the reporter protein, GFP expression is tested against progressively smaller subsets of the compound, nucleic acid, or protein pool until a single compound, nucleic acid, or protein or minimal effective number thereof is demonstrated to increase GFP expression. Such a compound (e.g., a cDNA encoding a protein capable of activating 7b2 gene transcription) is useful for treating or alleviating the symptoms of hypoglycemia or a hypercortisolism disorder such as Cushing's disease.

Compounds may also be screened for an ability to increase 7b2 protein activity, such as an ability of 7b2 to be secreted, or an ability of 7b2 to interact with PC2. Such a compound may be tested, for example, in the 7b2-PC2 interaction assays previously described (see, e.g., Braks and Martens, Cell 78: 263–273, 1994; Zhu and Lindberg, J. Cell. Biol. 129: 1641–1650, 1995). Such a compound found to increase 7b2 protein activity is also useful to treat a hypercortisolism disorder or hypoglycemia, or to alleviate the symptoms of a hypercortisolism disorder or hypoglycemia.

(b) Methods and Reagents for Treating Hypocortisolism or Hyperglycemia

A compound that reduces the level of expression 7b2 protein, or inhibits transcription or translation of nucleic acid encoding the 7b2 protein may be administered to neuroendocrine cells or pituitary cells in patients suffering from a hypocortisolism disorder such as Addison's disease, or patients suffering from hyperglycemia. Such a compound may be identified as described above, with the desired compound for treating hyperglycemia or hypocortisolism being a compound that results in a decrease in expression in a cell of a reporter gene operably linked to a 7b2 gene promoter as compared to an untreated cell.

One example of a useful compound for treating (or alleviating the symptoms of) hyperglycemia or hypocortisolism by inhibiting 7b2 expression is antisense 7b2 nucleic acid. An antisense 7b2 nucleic acid is sufficiently complementary to a region of the coding strand of the 7b2-encoding gene or RNA to allow hybridization and concomitant reduction in the transcription or translation of the gene in vivo. Preferably the antisense 7b2 nucleic acid is at least 25 nucleotides in length, more preferably at least 50 nucleotides in length, even more preferably at least 75 nucleotides in length, and most preferably at least 100 nucleotides in length. Preferably, the reduction is at least 25%, more preferably, at least 50%, even more preferably, at least 75%, and most preferably, an antisense 7b2 nucleic acid reduces the transcription or translation of a 7b2-encoding gene or RNA by 100% (i.e., completely inhibits transcription or translation).

Another example of a useful compound for treating (or alleviating the symptoms of) hyperglycemia or hypocortisolism by inhibiting the 7b2 protein is a 7b2 protein-specific neutralizing antibody. Such a neutralizing antibody may be generated by standard techniques (see, e.g., Ausubel et al., supra) and may be a polyclonal or monoclonal antibody. The utility of such an antibody is that it neutralizes or inhibits the 7b2 protein. The 7b2 protein-specific neutralizing antibody may interferes with any of the biological activities of a 7b2 protein. The antibody may inhibit the expression of the 7b2 protein, the secretion of the protein, or the ability of the 7b2 protein to interact with PC2. Preferably, the 7b2 neutralizing antibody reduces a biological activity of 7b2 by at least 25%, more preferably by at least 50%, and even more preferably by 70%, and most preferably by 100%.

Yet another example of compounds useful for treating (or alleviating the symptoms of) hyperglycemia or hypocortisolism that work by inhibiting the 7b2 protein are polypeptide fragments of the 7b2 protein. For example, a 7b2 polypeptide fragment that binds to PC2 and, thus inhibits the interaction of full length 7b2 with PC2, will inhibit biological activity of the 7b2 protein. Such polypeptide fragments can be readily identified by setting up an in vitro binding interaction of PC2 with full length 7b2, and then adding 7b2 fragments to the interaction. A 7b2 fragment that is able to compete with full length 7b2 for the 7b2-binding site of PC2 will result in the release of full length 7b2 from the interaction (see, e.g., the assays described in Braks and Martens, Cell 78: 263–273, 1994; and Zhu and Lindberg, J. Cell. Biol. 129: 1641–1650, 1995). The detection of full length 7b2 release may be facilitated by detectably-labelling full length 7b2 by, for example, making an N- or C-terminal fusion of full-length 7b2 with GFP. Such a 7b2 fragment found to inhibit the PC2-binding activity of full length 7b2 may be administered to patients suffering from hyperglycemia or hypocortisolism to alleviate the disease symptoms.

Test Compounds

In general, drugs for prevention or treatment of an endocrine disorder which function by altering the amount or level of biological activity of a 7b2 protein are identified from libraries of natural products or synthetic (or semi-synthetic) extracts or chemical libraries according to methods known in the art. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Libraries of genomic DNA or cDNA may be generated by standard techniques (see, e.g., Ausubel et al., supra) and are also commercially available (Clontech Laboratories Inc., Palo Alto, Calif.). Nucleic acid libraries used to screen for compounds that alter 7b2 gene expression or 7b2 protein activity are not limited to the species from which the 7b2 gene or protein is derived. For example, a Xenopus cDNA may be found to encode a protein that alters human 7b2 gene expression or alters human 7b2 protein activity.

Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods.

In addition, methods for dereplication (e.g., taxonomic dereplication, biological dereplication, and chemical dereplication, or any combination thereof) or the elimination of replicates or repeats of materials already known for their therapeutic activities for neuroendocrine or pituitary disorders should be employed whenever possible.

When a crude extract is found to prevent or delay onset of an endocrine disorder, further fractionation of the positive lead extract is necessary to isolate chemical constituents responsible for the observed effect. Thus, the goal of the extraction, fractionation, and purification process is the characterization and identification of a chemical entity within the crude extract having endocrine disorder-preventative or -palliative activities. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed in the 7b2 null mouse described herein to determine if they can alleviate or exacerbate the symptoms of the diseased animal.

Administration of Reagents that Alter 7b2 Expression or Function

A 7b2 protein, a 7b2-encoding DNA, or a 7b2 expression- or function-altering compound may be administered within a pharmaceutically-acceptable diluent, carrier, or excipient, in unit dosage form to patients suffering from an endocrine disorder. Administration may begin before or after the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intrathecal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington's Pharmaceutical Sciences* ($18^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for 7b2 protein, 7b2 gene, or 7b2 expression- or function-enhancing compound compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

All publications mentioned in this specification are herein incorporated by reference to the same extent as if each independent publication was specifically and individually indicated to be incorporated by reference.

---

What is claimed is:

1. A method for targeting heterologous DNA to integrate into an exon of a eukaryotic cell, said method comprising the steps of:
(a) generating a pool of bacteria containing plasmids into which have been randomly integrated a transposon comprising said heterologous DNA;
(b) isolating from said pool a bacterium which contains a plasmid into which said transposon is integrated into a copy of said exon on said plasmid by assessing PCR amplification products generated from said pool using primers specific for said exon;
(c) introducing said plasmid of said bacterium into said cell under conditions that promote homologous recombination; and
(d) screening genomic DNA of said cell for integration of said heterologous DNA into said exon of said cell.

2. The method of claim 1, wherein said transposon bears at its extremities recognition sequences of a first rare cutting restriction endonuclease, which recognition sequences of said first rare cutting restriction endonuclease are absent in said exon.

3. The method of claim 1, wherein said heterologous DNA, or portion thereof, encodes a selectable marker protein.

4. The method of claim 3, wherein said heterologous DNA, or portion thereof, additionally encodes a second protein, or polypeptide fragment thereof.

5. The method of claim 3, wherein said marker protein is a prokaryotic selectable marker protein.

6. The method of claim 5, wherein said prokaryotic selectable marker protein is replaced by a eukaryotic selectable marker protein via said recognition sequences of said first rare-cutting restriction endonuclease.

7. The method of claim 6, wherein said prokaryotic selectable marker protein is additionally replaced with DNA, or a portion thereof, encoding a second protein, or polypeptide fragment thereof.

8. The method of claim 1, wherein said exon copy or portion thereof has at its borders destroyed recognition sequences of a second rare cutting restriction endonuclease.

9. The method of claim 8, wherein said genomic DNA is digested with said second rare-cutting restriction endonuclease.

10. The method of claim 1 or 9, wherein said screening is carried out by Southern blot analysis of said genomic DNA with a detectable probe specific for said exon.

11. The method of claim 1 or 9, wherein said screening is by PCR amplification of said genomic DNA with primers specific for said exon.

12. The method of claim 1, wherein said integration of said heterologous DNA into said exon results in a reduced level of expression of the gene product of said exon.

13. The method of claim 1, wherein said integration of said heterologous DNA into said exon results in the expression of a truncated gene product of said exon.

14. The method of claim 1, wherein said integration of said heterologous DNA into said exon results in the expression of a fusion gene product of said exon and said heterologous DNA, or portion thereof.

15. The method of claim 1, wherein said integration results in expression of a product encoded by said heterologous DNA, or portion thereof.

16. The method of claim 15, wherein said heterologous DNA, or portion thereof, encodes a fusion protein.

17. A method for making a chimeric mouse containing heterologous DNA, said method comprising:
   (a) producing an embryonal cell of said mouse with a targeted exon according to the following steps:
      (i) generating a pool of bacteria containing plasmids into which have been randomly integrated a transposon including heterologous DNA;
      (ii) isolating from said pool a bacterium which contains a plasmid into which said transposon is integrated into a copy of said exon on said plasmid by assessing PCR amplification products generated from said pool using primers specific for said exon;
      (iii) introducing said plasmid of said bacterium into said embryonal cells under conditions that promote homologous recombination; and
      (iv) screening genomic DNA of said embryonal cells to identify an embryonal cell in which there has occurred integration of said heterologous DNA into said exon; and
   (b) placing said embryonal cell into a murine blastocyst and transplanting said blastocyst into a recipient animal such that said chimeric mouse is produced.

18. The method of claim 17, wherein said transposon bears at its extremities recognition sequences of a first rare cutting restriction endonuclease, which recognition sequences of said first rare cutting restriction endonuclease are absent in said exon.

19. The method of claim 17, wherein said heterologous DNA, or portion thereof, encodes a selectable marker protein.

20. The method of claim 19, wherein said heterologous DNA, or portion thereof, additionally encodes a second protein, or polypeptide fragment thereof.

21. The method of claim 19, wherein said marker protein is a prokaryotic selectable marker protein.

22. The method of claim 21, wherein said prokaryotic selectable marker protein is replaced by a eukaryotic selectable marker protein via said recognition sequences of said first rare-cutting restriction endonuclease.

23. The method of claim 22, wherein said prokaryotic selectable marker protein is additionally replaced with DNA, or a portion thereof, encoding a second protein, or polypeptide fragment thereof.

24. The method of claim 17, wherein said exon copy or portion thereof has at its borders destroyed recognition sequences of a second rare cutting restriction endonuclease.

25. The method of claim 24, wherein said genomic DNA is digested with said second rare-cutting restriction endonuclease.

26. The method of claim 17 or 25, wherein said screening is carried out by Southern blot analysis of said genomic DNA with a detectable probe specific for said exon.

27. The method of claim 17 or 25, wherein said screening is by PCR amplification of said genomic DNA with primers specific for said exon.

28. The method of claim 17, wherein said animal expresses a reduced level of the protein encoded by the gene of said exon.

29. The method of claim 17, wherein said animal expresses a truncated protein encoded by the gene of said exon.

30. The method of claim 17, wherein said animal expresses a fusion protein product encoded by the gene of said exon and said heterologous DNA, or portion thereof.

31. The method of claim 17, wherein said animal expresses a product encoded by said heterologous DNA, or portion thereof.

32. The method of claim 31, wherein said heterologous DNA, or portion thereof, encodes a fusion protein.

* * * * *

UNITED STATES PATENT AND TRADEMARK OFFICE
CERTIFICATE OF CORRECTION

PATENT NO. : 6,504,081 B1
DATED : January 7, 2003
INVENTOR(S) : Westphal et al.

It is certified that error appears in the above-identified patent and that said Letters Patent is hereby corrected as shown below:

Title page,
Item [56], References Cited, OTHER PUBLICATIONS, "Steiner et al." reference, "Emymology" should read -- Enzymology --.
"Zhu and Lindberg" reference, "Ezymatic" should read -- Enzymatic --.

Column 13,
Line 13, "the the Zeocin$^{TM}$" should be -- the Zeocin$^{TM}$ --.

Column 16,
Line 56, "commercialy" should be -- commercially --.

Column 19,
Line 64, "7B2" should be -- 7b2 --.

Signed and Sealed this

Twenty-fourth Day of August, 2004

JON W. DUDAS
*Director of the United States Patent and Trademark Office*